United States Patent
Ren et al.

(10) Patent No.: US 9,618,521 B2
(45) Date of Patent: Apr. 11, 2017

(54) SPERM-SPECIFIC CATION CHANNEL, CATSPER2, AND USES THEREFOR

(71) Applicants: Children's Medical Center Corporation, Boston, MA (US); Board of Regents, The University of Texas System, Austin, TX (US)

(72) Inventors: Dejian Ren, Wynnewood, PA (US); David Clapham, Wellesley, MA (US); David L. Garbers, Denton, TX (US); Timothy A. Quill, Grapevine, TX (US)

(73) Assignees: Children's Medical Center Corporation, Boston, MA (US); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 14/249,990

(22) Filed: Apr. 10, 2014

(65) Prior Publication Data
US 2014/0363813 A1    Dec. 11, 2014

Related U.S. Application Data

(60) Division of application No. 12/021,474, filed on Jan. 29, 2008, now Pat. No. 8,729,248, which is a division of application No. 10/828,975, filed on Apr. 21, 2004, now Pat. No. 7,339,029, which is a continuation of application No. PCT/US02/33676, filed on Oct. 22, 2002.

(60) Provisional application No. 60/345,324, filed on Oct. 22, 2001.

(51) Int. Cl.
| | |
|---|---|
| *G01N 33/53* | (2006.01) |
| *G01N 33/68* | (2006.01) |
| *C07K 14/705* | (2006.01) |
| *C12Q 1/68* | (2006.01) |
| *A61K 35/12* | (2015.01) |
| *A61K 38/17* | (2006.01) |
| *C07K 14/47* | (2006.01) |
| *A61K 38/00* | (2006.01) |

(52) U.S. Cl.
CPC .......... *G01N 33/689* (2013.01); *A61K 35/12* (2013.01); *C07K 14/705* (2013.01); *C12Q 1/6881* (2013.01); *A61K 38/00* (2013.01); *A61K 38/177* (2013.01); *C07K 14/4715* (2013.01); *Y10S 530/852* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 5,459,039 A | 10/1995 | Modrich et al. |
| 5,498,531 A | 3/1996 | Jarrell |
| 6,159,478 A | 12/2000 | Haanes et al. |
| 6,787,309 B2 | 9/2004 | Splawski et al. |
| 7,339,029 B2 | 3/2008 | Ren et al. |
| 8,729,248 B2 | 5/2014 | Ren et al. |
| 2001/0039335 A1 | 11/2001 | Jacobs et al. |
| 2002/0082210 A1 | 6/2002 | Curtis |

FOREIGN PATENT DOCUMENTS

| | | |
|---|---|---|
| WO | WO-00/61624 | 10/2000 |
| WO | WO-00/66735 | 11/2000 |
| WO | WO-01/07611 | 2/2001 |
| WO | WO-01/54477 | 8/2001 |
| WO | WO-01/75067 | 10/2001 |
| WO | WO-01/88090 | 11/2001 |
| WO | WO-01/90304 | 11/2001 |
| WO | WO-01/90304 A2 | 11/2001 |
| WO | WO-02/090567 | 11/2002 |
| WO | WO-03/089583 | 10/2003 |
| WO | WO-03/091434 | 11/2003 |
| WO | WO-03/099865 | 12/2003 |

OTHER PUBLICATIONS

Quill et al., "A voltage-gated ion channel expressed specifically in spermatozoa," Proc. Natl. Acad. Sci. vol. 98, No. 22, 12572-12531.*
Lobley et al., Reprod. Biol. Endocrinol. Aug. 1, 2003 1:53, 15 pages.*
Singh et al., Reprod Biomed Online. Jan. 2015;30(1):28-38. doi: 10.1016/j.rbmo.2014.09.014. Epub Oct. 8, 2014.*
Ren et al., Physiology (Bethesda). Jun. 2010;25(3):165-75. doi: 10.1152/physiol.00049.2009.*
Arnoult et al., "Activation of mouse spterm T-type Ca2+ channels by adhesion to the egg zona pellucida," Proc. Natl. Acad. Sci. USA, vol. 92, pp. 13004-13009 (1996).
Avidan, Nili et al. "CATSPER2, A Human Autosomal Nonsyndromic Male Infertility Gene." European Journal of Human Genetics. Feb. 12, 2003. vol. 11. pp. 497-502.
Bedford, "Mammalian Fertilization Misread? Sperm Penetration of the Eutherian Zona Pellucida is Unlikely to be a Lytic Event," Biology of Reproduction, vol. 59, pp. 1275-1087 (1998).

(Continued)

*Primary Examiner* — Michael Szperka
(74) *Attorney, Agent, or Firm* — Wilmer Cutler Pickering Hale and Dorr LLP

(57) ABSTRACT

Nucleic acid and protein sequences relating to a cation channel which is sperm-specific (CatSper2) are disclosed. The CatSper2 protein is shown to be specifically expressed in sperm. Nucleic acids, vectors, transformed cells, transgenic animals, polypeptides, and antibodies relating to the CatSper2 gene and protein are disclosed. Also provided are methods of in vitro fertilization and contraception, methods of identifying modulators of CatSper2 activity, methods of genotyping subjects with respect to CatSper2, methods of diagnosing and treating CatSper2-mediated disorders, including infertility, as well as methods of doing business related to CatSper2-mediated disorders.

7 Claims, 1 Drawing Sheet

(56) References Cited

OTHER PUBLICATIONS

Chan H.C., Cation and anion channels in rat and human spermatozoa, Biochimica et Biophysica Acta, vol. 1323; pp. 117-129 (1997).
Colman, P.M., "Effects of amino acid sequence changes on antibody-antigen interactions," Research in Immunology, vol. 145; pp. 33-36 (1994).
Darszon et al., "Ion Channels in Sperm Physiology," Physiological Reviews, vol. 79, No. 2, pp. 481-510 (1999).
Database EMBL, Dec. 1, 2001 XP002306737, Database Accession No. Q96P76.
Database EMBL, Dec. 1, 2001, XP002306739, Database Accession No. Q91ZR5.
Database EMBL, Dec. 2, 2000, XP002314901, Database Accession No. BF436942.
Database EMBL, Feb. 13, 2002, XP002314905, Database Accession No. AAS90759.
Database EMBL, Jan. 25, 2001, XP002314968, Database Accession No. BF934163.
Database EMBL, Jun. 8, 2000, XP002314899, Database Accession No. AW971983.
Database EMBL, Mar. 2, 2000, XP002314904 Database Accession No. AW472972.
Database EMBL, Mar. 25, 2004, XP002314912, Database Accession No. ACN41330.
Database EMBL, Mar. 3, 2000, XP002314900, Database Accession No. AA662668.
Database EMBL, Mar. 3, 2000, XP002314902, Database Accession No. AA574312.
Database EMBL, Mar. 30, 2000, XP002306735, Database Accession No. AA416682.
Database EMBL, Mar. 30, 2000, XP002306736, Database Accession No. AA416577.
Database EMBL, Mar. 4, 2000, XP002314903, Database Accession No. AW197851.
Database EMBL, May 30, 2000, XP002306734, Database Accession No. AP000586.
Database EMBL, May 9, 2001, XP002314908, Database Accession No. BG718343.
Database EMBL, May 9, 2001, XP002314909, Database Accession No. BG718245.
Database EMBL, Nov. 29, 2001, XP002314910, Database Accession No. ABL90376.
Database EMBL, Nov. 29, 2001, XP002314911, Database Accession No. ABB89967.
Database EMBL, Oct. 15, 2001, XP002306738, Database Accession No. AF407333.
Database EMBL, Oct. 15, 2001, XP002306740, Database Accession No. AF407332.
Database EMBL, Oct. 8, 2001, XP002314898, Database Accession No. BF092492.
Database EMBL, Oct. 8, 2001, XP002314906, Database Accession No. BI826910.
Database EMBL, Oct. 8, 2001, XP002314907, Database Accession No. BI829451.
Garbers, D.L., "Ion channels. Swimming with sperm," Nature. vol. 413, No. 685, pp. 579, 581-582 (2001).
Hillier et al., (1997) Accession No. AA416577.1. Accessed Oct. 29, 2010 at HTTp://www.nbci.nlm.nih.gov/nucest/AA416577.1?report=gbwithparts&log$=seqview.
Hillier et al., Accession No. AA41682.1 (1997).
Hyne et al., "Calcium-dependent increase in adenosine 3', 5'-monophosphate and induction of the acrosome reaction in guinea pig spermatozoa," Proc. Natl. Acad. Sci. USA, vol. 76, No. 11, pp. 5699-5703 (1979).
Jin et al., "Catsper3 and Catsper4 encode two cation channel-like proteins exclusively expressed in the testis," Biology of Reproduction, vol. 73, pp. 1235-1242 (2005).
Jungnickel, M. K. et al., "Trp2 regulates entry of $Ca^{2+}$ into mouse sperm triggered by egg ZP3," Nature Cell Biology, vol. 3, pp. 499-502 (May 2001).
Lehmann-Horn et al., "Voltage-Gated Ion Channels and hereditary disease," Physiol Rev, vol. 79(4), pp. 1317-1372 (1999).
Lobley, Anna et al. "Identification of Human and Mouse CatSper3 and CatSper4 Genes: Characterisation of a Common Interaction Domain and Evidence for Expression in Testis." Reproductive Biology and Endocrinology. BioMed Central. London, UK. Aug. 1, 2003 1:53. 15 pages.
Martelange et al., "Identification on a Human Sarcoma of two new genes with tumor-specific expression," Cancer Research, vol. 60, pp. 3848-3855 (2000).
N.A., Suppl. 1, Trends Pharmacol. Sci., vol. 18, pp. 77-84 (1997).
Nikpoor et al., "CatSper gene expression in postnatal development of mouse testis and in subfertile men deficient sperm motility," human Reprod. vol. 19(1); pp. 124-128 (2004).
O'Toole, C. M. B. et al., "$CA^{2+}$ Entry through Store-operated Channels in Mouse Sperm is Initiated by Egg ZP3 and Drives the Aerosome Reaction," Molecular Biology of the Cell, vol. 11, pp. 1571-1584 (May 2000).
Quill et al., "A voltage-gated ion channel expressed specifically in spermatozoa," Proc. Natl. Acad. Sci. vol. 98, No. 22, 12572-12531 (2001).
Ren et al., "A Sperm Ion Channel Required for Sperm Motility and Male Fertility," Nature, vol. 413, No. 6856, Oct. 11, 2001, pp. 603-609 (2001).
Sanger Centre, "Genome Sequence of the Nematode C. elegans: A Platform for investigating Biology," Science, vol. 282, pp. 2012-2018 (1998).
Santi et al., "A dihydropyridine-sensitive T-type $Ca^{2+}$ current is the main $Ca^{2+}$ current carrier in mouse primary spermatocytes," American Journal of Physiology, vol. 271, pp. C1583-C1593 (1996).
Serrano et al., "Voltage-dependent CA2_channel subunit expression and immunolocalization in mouse spermatogenic cells and sperm," FEBS Letters, 462, pp. 171-176 (1999).
Skolnick et al., "From genes to protein structure and function: novel applications of computational approaches in the genomic era," Trends in Biotechnology, 2000, 18:34-39.
Strausberg R., *Homo sapiens*, Clone Image. Mar. 3, 2003, Database NCBI, Accession No. BD047442, pp. 1-3.
Tash, "Role of the cAMP, Calcium and Protein Phosporylation in Sperm Motility," In: Controls of Sperm Motility: Biological and Clinical Aspects, eds. Gagnon, pp. 229-240 (1990).
Wassarman, P. M. et al., "A profile of fertilization in mammals," Nature Cell Biology, vol. 3, pp. E59-E64 (Feb. 2001).
Watson et al., Recombinant DNA, 2nd Edition, W. H. Freeman and Company, p. 107, (1992).
Wennemuth et al., "Cav2.2 and Cav2.3 (N- and R-type) Ca2+ Channels in Depolarization-evoked Entry of Ca2+ into Mouse Sperm," The Journal of Biological Chemistry, vol. 275, No. 28, pp. 21210-21217 (2000).
Weyand et al., "Cloning and functional expression of a cyclic nucleotide-gated channel from mammalian sperm," Nature, vol. 386, pp. 859-863 (1994).
Whisstock et al., "Prediction of protein function from protein sequence and structure," Quarterly Review of Biophysics, 2003, 36:307-340.
Wiesner et al., "Cyclic Nucleotide-gated Channels on the Flagellum Control of Ca2+ Entry into Sperm," The Journal of Cell Biology, vol. 142, No. 2, pp. 473-484 (1998).
Yanigimachi, R., "Mammalian Fertilization," The Physiology of Reproduction, Second Edition, eds. Knobil and Neill, pp. 189-317, 130 pages (1994).

\* cited by examiner

A)

```
  1 MAQEQGHFQLLRADAIRSKLIDTFSLIEHLQGLSQAVPRHTLREILDPAY
 51 QQKLMSGDQEQLVRFSIKPRRMGHITHSRRLLSRLRVRCSRMPPLSLWAG
101 WVLDSSVFSKFIISLIFLNTFVLMVEIELMESTNTALWPVKLALEVADWF
                                                 S1
151 ILLSFIVEILIMWLASFSLFWKDAWNVFDFFVTLLSLLPELVVLLGVPAH
         S2                  S3
201 SVWLQLLRVCRVLRSLKLFARFRQIKVILLALVRALKSMTFLLMLLLIFF
       S4                              S5
251 YIFAVTGVYFFREYSRSTIEGLEYNMFFSDLLNSLVTVFILFTLDHWYAV
                                P
301 LQNIWKVPESSRVFSSIYVILWLLLGSIIFRNIIIAMMVTNFQNIRSELS
                    S6
351 EEMSHLEVQYKADMFKQQIIQRRQHSESLRGTSLGKVSEDIIETSDASDD
401 DDDDDDDDDDDDDDDDDKSDATESDGEESDSENSESENSESEKIDPEKDY
451 AKKSYPEKSHPEKSYPEKSHPEKSYPEKSHPEKSYDEQAEAEKVKEESKE
501 KAYPVSHSISSHGSIAADTAFLENLDWETLVHENLPGLMDMDQDDRIVWP
551 RDSLFRYFELLEKLQYNLEERKKLQEFAVQALMSFEDK
```

B)

```
Catsper 2   VL----DSSVFSKFIISLIFLNTFVLMVEIELMESTNTALWPVKLALEVADWFILLSFIV
              |    |  ||   |||  |        |       |        |     ||   |
Catsper 1   MILSLTQSLGPETFIFIVVCLNTVILVAQ-TFTELEIRGEW----YFMVLDSIFLSIYVL Catsper 2   EILLMWLASFSLFWKDAWNVFDFFVTLLSLLPELVVLLGVPAHSVW-LQLLRVCRVLRSL
             |    |         |   ||| |||       |               |   |  |  |
Catsper 1   EAVLKLIALGLEYFYDPWNNLDPFIMVMAVLDFVLLQINSLSYSFYNHSLFRILKVPKSM Catsper 2   KLFARFRQI-KVILLALVRALKSMTFLLMLLLIFFYIFAVTGVYFFREYSRSTIEGLEYN
             |        |          |              |     |       |
Catsper 1   RALRAIRVLRRLSILTSLHEVAGTLSQSLPSITAILTLMFTCLFLFSVVLRALFQDSDPK Catsper 2   MFFSDLLNSLVTVFILFTLDHWYAVLQNIWKVPESSRVFSSIYVILWLLLGSIIFRNIII
              |   ||| |||       |                 |              ||  |
Catsper 1   R-FQNIFTTLFTLFTMLTLDDWSLIY--IDNRAQGAWYIIPI-LMIYIVIQYFIFLNLVI Catsper 2   A-MM
            |
Catsper 1   AVLV
```

SPERM-SPECIFIC CATION CHANNEL, CATSPER2, AND USES THEREFOR

RELATED APPLICATIONS

This application is a divisional application of and claims benefit of priority to U.S. patent application Ser. No. 12/021,474, filed Jan. 29, 2008, which is a divisional application of and claims benefit of priority to U.S. patent application Ser. No. 10/828,975, filed Apr. 21, 2004, which is a national stage application of PCT/US02/33676, filed Oct. 22, 2002, which claims priority to U.S. provisional patent application No. 60/345,324, filed Oct. 22, 2001, all of which are hereby incorporated by reference in their entirety.

GOVERNMENT SUPPORT

The present invention was made, in part, with support from NIH Grant HD 36022. The U.S. government has certain rights in the invention.

BACKGROUND OF THE INVENTION

Field of the Invention

The present invention relates to the fields of molecular biology and reproductive technology. In particular, the invention relates to a cation channel protein expressed specifically in sperm cells, nucleic acids encoding the protein, cells engineered to express the protein, assays for compounds affecting the activity of the protein, and the use of such compounds in the treatment or causation of infertility, or as a means of contraception or animal control.

Description of the Related Art

Sperm and ova reciprocally interact in mammalian fertilization (Wassarman et al. (2001), *Nature Cell Biology* 3:E59-E64; Yanagimachi (1994), in *The Physiology of Reproduction*, Knobil & Neill eds. (Raven Press, New York), pp. 189-315). To reach the site of fertilization, sperm must travel relatively long distances and become primed for fertilization of the ova through capacitation and other processes. Once they arrive at the surface of an ovum, sperm interact with ovum extracellular matrix glycoproteins including the zona pellucida proteins. Sperm release acidic material during the acrosome reaction, a signaling event that presumably involves the opening of $Ca^{2+}$ channels and the influx of $Ca^{2+}$ into the sperm heads (O'Toole et al. (2000), *Mol. Biol. Cell* 11:1571-84). The TRPC2 protein, a putative $Ca^{2+}$-permeant channel, has recently been implicated in the acrosome reaction (Jungnickel et al. (2001), *Nat. Cell Biol.* 3:499-502). Penetration of sperm through the thick outer layer of the ovum is achieved through chemical lysis of the ovum coat and/or the mechanical motion of sperm (Bedford (1998), *Biol. Reprod.* 59:1275-87). Following infiltration of the ovum zona pellucida coat, the sperm membrane fuses with that of ovum. Fusion is followed by activation of the fertilization process, beginning with $Ca^{2+}$ oscillations in the ovum (Wassarman et al. (2001), supra; Yanagimachi (1994), in *The Physiology of Reproduction*, Knobil & Neill eds. (Raven Press, New York), pp. 189-315).

$Ca^{2+}$ and cyclic nucleotides control sperm motility (Tash (1990), in *Controls of Sperm Motility: Biological and Clinical Aspects*, Gagnon ed. (CRC Press, Boca Raton), pp. 229-240; Darszon et al. (1999), *Physiol. Rev.* 79:481-510; Hyne and Garbers (1979), *Proc. Natl. Acad. Sci. USA* 76:5699-703) and several voltage-dependent $Ca^{2+}$ channel ($Ca_V$) mRNAs and cyclic nucleotide-gated (CNG) channel proteins have been detected in sperm cell precursors (Darszon et al. (1999), *Physiol. Rev.* 79:481-510; Serrano et al. (1999), *FEBS Lett.* 462:171-6; Weyand et al. (1994) *Nature* 368:859-63; Wiesner et al. (1998), *J. Cell Biol.* 142:473-84). Furthermore, low voltage activated, dihydropyridine-sensitive "T-type" channels (Santi et al. (1996), *Am. J. Physiol.* 271):C1583-93; Arnoult et al. (1996), *Proc. Natl. Acad. Sci. USA* 93:13004-9) and pharmacologically defined N- and R-type currents have been measured in spermatogenic cells (Wennemuth et al. (2000). *J. Biol. Chem.* 275:21210-7). The role of these channels, however, in spermatogenesis or mature sperm function is not known.

Recently, a voltage-gated channel (CatSper1) was discovered that is required for normal fertility of mice (Ren et al. (2001), *Nature* 413:603-9).

SUMMARY OF THE INVENTION

In one aspect, the present invention provides isolated nucleic acids comprising all or a portion of a CatSper2 gene. In some embodiments, the isolated nucleic acids include a nucleotide sequence of at least 10, 12, 14, 16 or 18 consecutive nucleotides of SEQ ID NO: 1 or SEQ ID NO: 3 or SEQ ID NO: 5, or a sequence complementary thereto. In other embodiments, the nucleic acids include nucleotide sequences encoding a CatSper2 protein, at least a transmembrane domain of a CatSper2 protein, at least an extracellular loop of a CatSper2 protein, at least a pore region of a CatSper2 protein, at least an epitope of a CatSper2 protein having high predicted antigenicity, or a sequence complementary thereto. In particular embodiments, the nucleic acids include a sequence of SEQ ID NO: 1; a sequence of SEQ ID NO: 3; a sequence of SEQ ID NO: 5; a sequence encoding a polypeptide comprising approximately residues 104-126, 146-166, 176-195, 206-228, 241-262, and 316-340 of SEQ ID NO: 2; a sequence encoding a polypeptide comprising approximately residues 104-126, 146-166, 176-195, 206-228, 241-262, and 316-340 of SEQ ID NO: 4; a sequence encoding a polypeptide comprising approximately residues 102-124, 144-164, 174-193, 204-227, 239-260, and 314-338 of SEQ ID NO: 6; a sequence encoding a polypeptide comprising approximately residues 127-145, 196-205, and 263-315 of SEQ ID NO: 2; a sequence encoding a polypeptide comprising approximately residues 127-145, 196-205, and 265-315 of SEQ ID NO: 4; a sequence encoding a polypeptide comprising approximately residues 125-143, 194-203, and 261-313 of SEQ ID NO: 6; a sequence encoding a polypeptide comprising approximately residues 280-303 of SEQ ID NO: 2; a sequence encoding a polypeptide comprising approximately residues 280-303 of SEQ ID NO: 4; a sequence encoding a polypeptide comprising approximately residues 278-301 of SEQ ID NO: 6; a sequence encoding a polypeptide comprising approximately residues 266-275, 386-400, 447-458, and 482-494 of SEQ ID NO: 2; a sequence encoding a polypeptide comprising approximately residues 66-99, 266-275, and 394-414 of SEQ ID NO: 4; a sequence encoding a polypeptide comprising approximately residues 64-89, 262-275 and 562-588 of SEQ ID NO: 6; and a sequence complementary thereto. In certain embodiments, the invention provides nucleic acids comprising sequences that encode a polypeptide consisting essentially of approximately residues 266-275, 386-400, 447-458, and 482-494 of SEQ ID NO: 2; approximately residues 66-99, 266-275, and 394-414 of SEQ ID NO: 4; or approximately residues 64-89, 262-275 and 562-588 of SEQ ID NO: 6; and sequences complementary thereto.

In another aspect, the invention provides isolated nucleic acids encoding polypeptide having at least 80%, 85%, 90%, or 95% amino acid sequence identity with a CatSper2 protein; at least a transmembrane domain of a CatSper2 protein; at least an extracellular loop of a CatSper2 protein; and at least a pore region of a CatSper2 protein. In some embodiments, the isolated nucleic acids encode a polypeptide having at least 80%, 85%, 90% or 95% amino acid sequence identity with a CatSper2 protein and having CatSper2 activity in a cell capable of expressing CatSper2 activity.

In another aspect, the invention provides isolated nucleic acids that hybridize to at least a portion of a nucleic acid of SEQ ID NO: 1 or SEQ ID NO: 3 or SEQ ID NO: 5 under conditions including a wash step of 1.0×SSC at 65° C., a wash step of 0.5×SSC, a wash step of 0.2×SSC, or a wash step of 0.1×SSC. In some embodiments, the isolated nucleic acids encode a polypeptide having CatSper2 activity.

In another aspect, the invention provides nucleic acid comprising a nucleotide sequence encoding a polypeptide having CatSper2 activity, and that hybridizes to at least a portion of a nucleic acid of SEQ ID NO: 1 or SEQ ID NO: 3 or SEQ ID NO: 5 under conditions including a wash step of 1.0×SSC at 65° C., a wash step of 0.5×SSC, a wash step of 0.2×SSC, or a wash step of 0.1×SSC; and that is operably joined to a heterologous regulatory region such that the sequence is expressed. In another embodiment, the invention provides a nucleic acid comprising a nucleotide sequence encoding a polypeptide having at least 80%, 85%, 90% or 95% amino acid sequence identity with an amino acid sequence of SEQ ID NO: 2 or SEQ ID NO: 4 or SEQ ID NO: 6; and is operably joined to a heterologous regulatory region such that the sequence is expressed.

In another aspect, the invention provides a kit for detecting at least a portion of a CatSper2 nucleic acid. The kits can include any of the foregoing isolated nucleic acids of the invention, and a means for detecting the isolated nucleic acid. In some embodiments, the means for detecting the isolated nucleic acid includes a detectable label bound thereto and, in some embodiments, the means includes a labeled secondary nucleic acid which specifically hybridizes to the first isolated nucleic acid.

In another aspect, the invention provides a vector including any of the foregoing isolated nucleic acids of the invention. In some embodiments, the vector includes a genetic construct capable of expressing the nucleic acids of the invention. In some embodiments, the nucleic acids of the invention are operably joined to an exogenous regulatory region and, in some embodiments, the nucleic acids are operably joined to heterologous coding sequences to form a fusion vector. In some embodiments, the vector includes a CatSper2 regulatory region and, in some embodiments, the CatSper2 regulatory region is operably joined to a heterologous coding sequence.

In another aspect, the invention provides cells transformed with the foregoing nucleic acids of the invention, or a genetic construct capable of expressing a nucleic acid of the invention. In some embodiments, the nucleic acid of the invention is operably joined to heterologous coding sequences to encode a fusion protein. In some embodiments, the cells are bacterial cells, yeast cells, insect cells, nematode cells, amphibian cells rodent cells, or human cells. In some embodiments, the cells are mammalian somatic cells, fetal cells, embryonic stem cells, zygotes, gametes, germ line cells and transgenic animal cells.

In another aspect, the invention provides non-human transgenic animals. In these aspects, a genetic construct has introduced a modification into a genome of the animal, or an ancestor of the animal, and the modification includes insertion of a nucleic acid encoding at least a fragment of a CatSper2 protein, inactivation of an endogenous CatSper2 gene, or insertion by homologous recombination of a reporter gene operably joined to CatSper2 regulatory elements. In some embodiments, the modification is insertion of nucleic acid encoding a CatSper2 protein, at least a transmembrane domain of a CatSper2 protein, at least an extracellular loop of a CatSper2 protein, at least a pore region of a CatSper2 protein, or at least an epitope of a CatSper2 protein having high predicted antigenicity. In some embodiments, the animals are rats, mice, hamsters, guinea pigs, rabbit, dogs, cats, goats, sheep, pigs, and non-human primates.

In another aspect, the invention provides substantially pure protein preparations including polypeptides selected from a CatSper2 protein; at least a transmembrane domain of a CatSper2 protein; at least an extracellular loop of a CatSper2 protein, at least a pore region of a CatSper2 protein; and at least an epitope of a CatSper2 protein having high predicted antigenicity. In particular embodiments, the polypeptide is selected from SEQ ID NO: 2; SEQ ID NO: 4; SEQ ID NO: 6; a sequence encoding a polypeptide comprising approximately residues 104-126, 146 166, 176-193, 206-228, 241-262, and 316-340 of SEQ ID NO: 2; a sequence encoding a polypeptide comprising approximately residues 104-126, 146-165, 176-195, 206-228, 241-262, and 316-340 of SEQ ID NO: 4; a sequence encoding a polypeptide comprising approximately residues 102-124, 144-164, 174-193, 204-227, 239-260, and 314-338 of SEQ ID NO: 6; approximately residues 127-145, 196-205, and 263-315 of SEQ ID NO: 2; approximately residues 127-145, 196-205, and 265-315 of SEQ ID NO: 4; approximately residues 125-443, 194-203, and 261-313 of SEQ ID NO: 6; approximately residues 280-303 of SEQ ID NO: 2; approximately residues 280-303 of SEQ ID NO: 4; approximately residues 278-301 of SEQ ID NO: 6; approximately residues 266-275, 386-400, 447-458, and 482-494 of SEQ ID NO: 2; approximately residues 66-99, 266-275, and 394-414 of SEQ ID NO: 4; and approximately residues 64-89, 262-275 and 562-588 of SEQ ID NO: 6. In certain embodiments, the invention provides substantially pure protein preparations including polypeptides consisting essentially of approximately residues 266-275, 386-400, 447-458, and 482-494 of SEQ ID NO: 2; approximately residues 66-99, 266-275, and 394-414 of SEQ ID NO: 4; or approximately residues 64-89, 262-275 and 562-588 of SEQ ID NO: 6.

In another aspect, the invention provides a substantially pure protein preparation including polypeptides having at least 80%, 85%, 90%, or 95% amino acid sequence identity with a CatSper2 protein; at least a transmembrane domain of a CatSper2 protein, at least an extracellular loop of a CatSper2 protein; or at least a pore region of a CatSper2 protein. In some embodiments, the substantially pure protein preparation includes a polypeptide having at least 80%, 85%, 90%, or 95% amino acid sequence identity with a CatSper2 protein and having CatSper2 activity in a cell capable of expressing CatSper2 activity.

In another aspect, the invention provides a substantially pure antibody preparation including an antibody raised against a CatSper2 epitope. In some embodiments, the epitope has high predicted antigenicity. In some embodiments, the epitope includes an amino acid sequence selected from within approximately residues 266-275, 386-400, 447-458, and 482-494 of SEQ ID NO: 2; approximately residues 66-99, 266-275, and 394-414 of SEQ ID NO: 4; or approximately residues 64-89, 262-275 and 562-588 of SEQ ID NO: 6. In some embodiments, the antibody is a monoclonal antibody. In some embodiments, the antibody is an Fab fragment, an F(ab')$_2$ fragment, an Fv fragment, or a single-chain Fv fragment (scFv).

In another aspect, the invention provides a kit for detecting at least an epitope of a CatSper2 protein. The kits include an anti-CatSper2 antibody of the invention and a means for detecting said antibody. In some embodiments, the means for detecting said anti-CatSper2 antibody includes a detectable label bound thereto and, in some embodiments, the means for detecting said anti-CatSper2 antibody includes a labeled secondary antibody which specifically binds to the anti-CatSper2 antibody.

In another aspect, the invention provides methods of identifying potential modulators of CatSper2 activity. The methods include contacting a candidate compound with a cell expressing a CatSper2 protein; measuring an indicator of CatSper2 activity in the cell; determining whether the candidate compound caused an increase or decrease in the indicator relative to a reference level; and identifying the candidate compound as a potential modulator of CatSper2 activity if the compound causes an increase or decrease in the indicator. In some embodiments, the indicator is an indicator of the level of mRNA encoding the CatSper2 protein, an indicator of the level of CatSper2 protein, an indicator of cation flux across a membrane of said cell, or an indicator of whole cell or channel currents of said cell. In some embodiments, the cell has been transformed with a genetic construct capable of expressing a CatSper2 protein. In some embodiments, the cell is a mature sperm cell and the indicator is a measure of sperm mobility.

In another aspect, the invention provides methods of identifying a potential modulator of CatSper2 activity comprising contacting a candidate compound with at least a structural domain of a CatSper2 protein; measuring binding, if any, between the candidate compound and the CatSper2 moiety; and identifying the candidate compound as a potential modulator of CatSper2 activity if the binding is significant. In some embodiments, the CatSper2 moiety is a CatSper2 protein; at least a transmembrane domain of a CatSper2 protein, at least an extracellular loop of a CatSper2 protein; or at least a pore region of a CatSper2 protein.

In another aspect, the invention provides a method of decreasing the fertility of a male subject by administering a compound to the subject which decreases CatSper2 activity. In another aspect, the invention provides a method of causing reversible infertility in a male subject by administering a compound to the subject which decreases CatSper2 activity. In another aspect, the invention provides a method of contraception in which a compound which decreases CatSper2 activity is administered to a male or female subject. In each of the foregoing embodiments, the compound can be in an injection, a transdermal patch, a bioerodable implant, a lubricant, a moisturizer, a foam, a jelly, or a sponge. If the subject is a female, the compound can be administered into at least one of the vagina, uterus or fallopian tubes. In each of the foregoing embodiments, the compound can be a nucleic acid which is antisense to at least a portion of a CatSper2 gene or an antibody to a CatSper2 protein, including an Fab fragment, an F(ab')$_2$ fragment, an Fv fragment, or an scFv fragment. In some embodiments, the subject is a mammal. In some embodiments, the subjects are humans, dogs, cats, cows, sheep, horses, mice, rats, raccoons, and gophers. In other embodiments, the subjects are fish, amphibians or insects. In related aspects, the invention provides for the use of a compound which decreases CatSper2 activity in the preparation of a medicament for decreasing the fertility of a male subject, or causing reversible infertility in a male subject, or in the preparation of a contraceptive for administration to a male or female. Thus, the invention provides contraceptive preparations including compounds which decrease CatSper2 activity, including nucleic acids which are antisense to at least a portion of a CatSper2 gene and antibodies to a CatSper2 protein.

In another aspect, the invention provides methods of diagnosing a CatSper2-related disorder in a mammal by determining the presence or absence of a mutation in a CatSper2 gene. In some embodiments, the presence or absence of differences between a determined nucleic acid or amino acid sequence and a reference sequence indicates the presence or absence of mutations in the CatSper2 gene. In some embodiments, the method includes contacting at least a fragment of the CatSper2 protein with an antibody known to bind to a CatSper2 protein in which a mutation is known to be present or absent and detecting binding between the antibody and the CatSper2 protein. In other embodiments, the method includes measuring an indicator of CatSper2 activity in a cell; and comparing the measured indicator to a reference level. The indicator can be an indicator of the level of mRNA encoding CatSper2 protein, an indicator of the level of CatSper2 protein, an indicator of cation flux across a membrane of said cell, or an indicator of whole cell or channel currents of said cell. In some embodiments, the disorder is CatSper2-related infertility. In another aspect, the invention provides methods of genotyping a subject with respect to a CatSper2 gene.

In another aspect, the invention provides a method of in vitro fertilization by sperm having decreased CatSper2 activity, decreased motility, or decreased ability to penetrate a zona pellucida, in which a zona pellucida is removed from at least one ovum; and the ovum is contacted with at least one sperm.

In another aspect, a method of treating a subject characterized by infertility due to decreased CatSper2 activity is provided. The method includes transforming sperm or sperm progenitors of the subject with a genetic construct capable of expressing a CatSper2 protein and using transformed sperm of said subject to fertilize an ovum. Alternatively, the method includes administering a CatSper2 protein to sperm or sperm progenitors of the subject.

In another aspect, the invention provides methods of diagnosing an anti-CatSper2 antibody-mediated infertility caused by anti-CatSper2 antibodies present in a female urogenital tract. In another aspect, methods of treating an anti-CatSper2 antibody-mediated infertility caused by anti-CatSper2 antibodies present in a female urogenital tract are provided.

In another aspect, the invention provides methods of conducting a drug discovery business including (a) identifying, by an assay of the invention, one or more agents which antagonize CatSper2 activity; (b) determining if an agent identified in step (a), or an analog thereof, inhibits at least one of sperm motility or egg penetrance; (c) conducting therapeutic profiling of an agent identified as an inhibitor in step (b) for efficacy and toxicity in one or more animal models; and (d) formulating a pharmaceutical preparation including one or more agents identified in step (c) as having an acceptable therapeutic profile. In some embodiments, the method further includes the step of establishing a system for distributing the pharmaceutical preparation for sale, and optionally including establishing a sales group for marketing the pharmaceutical preparation.

BRIEF DESCRIPTION OF THE DRAWINGS

The following drawing is illustrative of certain embodiments of the invention but is not meant to limit the scope of the invention.

FIG. 1 (A) Amino acid sequence of murine CatSper2. The transmembrane segments and ion selective P region are underlined. The basic residues of S4 are highlighted in bold. (B) Pair-wise alignment of CatSper2 and CatSper1 transmembrane regions. The P regions are boxed.

DETAILED DESCRIPTION

The present invention depends, in part, upon the identification, isolation and characterization of a novel voltage-gated ion channel (CatSper2) expressed in male germ calls, but not in other tissues tested, and which plays a significant role in the motility of sperm and their ability to fertilize ova. The protein has been designated CatSper2 to indicate that it is the second Cation channel which is Sperm-specific to be identified. The putative channel contains 6 transmembrane segments, a structure more similar to the voltage-gated potassium channels, but its ion selective pore indicates that it is a calcium channel. The mRNA is expressed during the meiotic or post-meiotic stages of spermatogenesis, and the protein is localized to the sperm flagellum, consistent with its role in the regulation of sperm motility. Therefore, inhibitors of the activity of the CatSper2 protein can be used as male and female contraceptives.

The patent, scientific and medical publications referred to herein establish knowledge that was available to those of ordinary skill in the art at the time the invention was made. The entire disclosures of the issued U.S. patents, published and pending patent applications, and other references cited herein are hereby incorporated by reference. In particular, the entire disclosure of U.S. Provisional Patent Appln. Ser. No. 60/345,324, filed Oct. 22, 2001, is incorporated herein by reference.

DEFINITIONS

All technical and scientific terms used herein, unless otherwise defined below, are intended to have the same meaning as commonly understood by one of ordinary skill in the art; references to techniques employed herein are intended to refer to the techniques as commonly understood in the art, including variations on those techniques or substitutions of equivalent techniques which would be apparent to one of skill in the art. In order to more clearly and concisely describe the subject matter which is the invention, the following definitions are provided for certain terms which are used in the specification.

As used herein, the term "CatSper2 protein" means a sperm-specific cation channel such as the human CatSper2 proteins disclosed in SEQ ID NO: 2 and SEQ ID NO: 4, human allelic and splice variants of the disclosed CatSper2 proteins, non-human mammalian homologs of these human CatSper2 proteins (e.g., SEQ ID NO: 6), and functional equivalents thereof. The term CatSper2 protein refers to naturally occurring proteins as isolated from sperm, recombinantly produced proteins from cells transformed with CatSper2 genes, and fusion proteins in which CatSper2 sequences are fused to N-terminal or C-terminal polypeptides. The term "CatSper2 fragment" refers to fragments of the CatSper2 proteins, such as structural domains and epitopes. A fragment of a CatSper2 protein comprises at least six amino acid residues.

As used herein, the term "CatSper2 gene" means a gene encoding a CatSper2 protein, including the human CatSper2 proteins disclosed in SEQ ID NO: 2 and SEQ ID NO: 4, human allelic and splice variants of the disclosed CatSper2 proteins, non-human mammalian homologs of these human CatSper2 proteins (e.g., SEQ ID NO: 6), and functional equivalents thereof. The term CatSper2 gene refers to both naturally occurring genes as isolated from genomic DNA, and recombinantly produced genes in which the CatSper2 coding regions are operably joined to either endogenous or exogenous regulatory elements, with or without intron sequences, and with or without 5' or 3'-flanking sequences which can encode heterologous (i.e., non-CatSper2) sequences to form a CatSper2 fusion protein. A CatSper2 gene will include, at a minimum, a coding region encoding the protein operably joined to regulatory elements (e.g., promoter, enhancer) which allow transcription of the coding region to mRNA which can be translated into a CatSper2 protein.

As used herein "CatSper2" activity means any normal biological activity of a wild type CatSper2 protein when expressed in a cell or cell type in which CatSper2 is normally expressed and under conditions under which CatSper2 is normally expressed. Such activity can include induction of an ion current; mediation of cAMP-induced $Ca^{2+}$ influx; restoration of sperm motility when expressed in CatSper2−/− sperm; and/or restoration of the ability to penetrate eggs when expressed in CatSper2−/− sperm. CatSper2 activity can be measured in sperm cells or spermatocytes, or in other cells in which any necessary accessory factors are present.

As used herein with respect to nucleic acid and amino acid sequences, the term "identity" means a measure of the degree of similarity of two sequences based upon an alignment of the sequences which maximizes identity and which is a function of the number of identical nucleotides or residues, the number of total nucleotides or residues, and the presence and length of gaps in the sequence alignment. A variety of algorithms and computer programs are available for determining sequence identity using standard parameters. For example, Gapped BLAST or PSI-BLAST (Altschul et al. (1997), *Nucleic Acids Res.* 25:33 89-3402), BLAST (Altschul et al. (1990), *J. Mol Biol.* 215:403-410), and Smith-Waterman (Smith et al. (1981), *J. Mol. Biol.* 147:195-197). As stated herein, percent identity is based upon the default values for the BLAST algorithms.

As used herein, the term "homolog" means a protein which is evolutionarily-related to and shares substantial, conserved structural and functional similarity with a reference protein, but which is naturally present in a different species (e.g., human, rat and insect CatSper2 proteins are homologs of each other).

As used herein, the term "mutation" refers to a change in a nucleic acid sequence, whether or not expressed as a change in a corresponding encoded protein sequence, relative to some reference sequence. The reference sequence can be a "wild-type" sequence (i.e., one or more high frequency sequences in a population corresponding to a "normal" phenotype), or any other sequence. As used herein, the term mutation is intended to be synonymous with the term polymorphism, and therefore the differences between any two non-identical sequences can be regarded as mutations. The term mutation is intended to encompass insertions, deletions and/or substitutions of one or more nucleotides relative to a reference sequence.

As used herein, the terms "exogenous" or "heterologous" mean, with respect to two or more genetic sequences, that the genetic sequences do not occur in the same physical relation to each other in nature and/or do not naturally occur within the same genome. For example, a genetic construct can include a coding region which is operably joined to one or more regulatory elements, and these sequences are considered heterologous to each other if they are not operably joined in nature and/or they are not found in the same genome in nature. Similarly, a genetic construct which is introduced into a cell is considered heterologous to that cell to the extent that it contains genetic sequences not found in that cell. In addition, a synthetically-produced genetic sequence based upon a naturally occurring sequence, will be heterologous to the naturally-occurring sequence to the extent the sequence has been altered and the synthetic sequence does not exist in nature. Allelic variants of a sequence in a species are not considered heterologous to each other.

As used herein, the term "operably joined" refers to a covalent and functional linkage of genetic regulatory elements and a genetic coding region which can cause the coding region to be transcribed into mRNA by an RNA polymerase which can bind to one or more of the regulatory elements. Thus, a regulatory region, including regulatory elements, is operably joined to a coding region when RNA polymerase is capable under permissive conditions of binding to a promoter within the regulatory region and causing transcription of the coding region into mRNA. In this context, permissive conditions would include standard intracellular conditions for constitutive promoters, standard conditions and the absence of a repressor or the presence of an inducer for repressible/inducible promoters, and appropriate in vitro conditions, as known in the art, for in vitro transcription systems.

As used herein, the term "expression" refers to the process by which a coding sequence of a gene is transcribed into a primary mRNA transcript, the primary mRNA transcript is processed into a mature mRNA, and the mature mRNA is translated into a protein. Expression can optionally include post-translation modifications of the resulting polypeptide.

As used herein, the phrase "genetic construct encoding a CatSper2 protein" means a recombinant DNA, RNA, DNA-RNA hybrid, or nucleic acid analog molecule which includes a genetic sequence encoding, or which is complementary to a genetic sequence encoding, or which is complementary to a genetic sequence encoding, the amino acid sequence of the CatSper2 protein, and which is capable of being expressed in a cell which has been transformed with the construct. The construct can express the CatSper2 protein transiently, or can stably integrate into the genome of the cell and express the protein conditionally or constitutively.

As used herein, the term "vector" means any genetic construct, such as plasmid, phage, transposon, cosmid chromosome, virus, virion, etc., which is capable of transferring gene sequences between cells. Vectors are capable of one or more of replication, expression, and insertion or integration, but need not possess each of these capabilities. Thus, the term includes cloning, expression, homologous recombination, and knock-out vectors.

As used herein, with respect to genetic engineering, the term "transform" means to introduce into a cell or an organism an exogenous nucleic acid or nucleic acid analog which replicates within that cell or organism, that encodes a polypeptide sequence which is expressed in that cell or organism, and/or that is integrated into the genome of that cell or organism so as to affect the expression of a genetic locus. The term "transform" is used to embrace all of the various methods of introducing such nucleic acids or nucleic acid analogs, including, but not limited to the methods referred to in the art as transformation, transfection, transduction, electroporation, ballistic injection, and the like.

As used herein, a "nucleic acid analog" means a molecule having sufficient structural and functional similarity to a nucleic acid to direct sequence-specific forward or reverse transcription of complementary nucleic acids, or to direct sequence-specific translation of an encoded polypeptide within a living cell. As used herein, whenever the term "nucleic acids" is used, the term is intended to embrace nucleic acid analogs when such analogs would be useful or suitable in the context of the usage.

As used herein, the term "reporter gene" means any genetic sequence which, when expressed, has a biochemical or phenotypic effect which is detectable. Reporter genes are also known in the art as "marker" genes.

As used herein, the term "antibody" is intended to embrace naturally produced antibodies, recombinantly produced antibodies, and antibody fragments such as Fab fragments, $F(ab')_2$ fragments, Fv fragments, and single-chain Fv fragment (scFv).

As used herein, the term "effective amount" of an agonist or antagonist, or an enhancer or repressor, means the total amount of the active component(s) of a composition that is sufficient to cause a statistically significant change of a detectable biochemical or phenotypic characteristic. When applied to an individual active ingredient, administered alone, the term refers to that ingredient alone. When applied to a combination, the term refers to combined amounts of the active ingredients that result in the effect, whether administered in combination, serially or simultaneously.

As used herein, the term "substantially pure" means a preparation which contains at least 60% (by dry weight) of the protein of interest, exclusive of the weight of other intentionally included compounds. In certain embodiments, the preparation is at least 75%, at least 90%, or at least 99% the protein of interest by dry weight, exclusive of the weight of other intentionally included compounds. Purity can be measured by any appropriate method, e.g., column chromatography, gel electrophoresis, amino acid compositional analysis or HPLC analysis. If a preparation intentionally includes two or mote different proteins of the invention, a "substantially pure" preparation means a preparation in which the total dry weight of the proteins of the invention is at least 60% of the total dry weight, exclusive of the weight of other intentionally included compounds. For preparations containing two or more proteins of the invention, the total weight of the proteins of the inventions should be at least 75%, at least 90%, or at least 99%, of the total dry weight of the preparation, exclusive of the weight of other intentionally included compounds. Thus, if the proteins of the invention are mixed with one or more other compounds (e.g., diluents, stabilizers, detergents, excipients, salts, sugars, lipids) for purposes of administration, stability, storage, and the like, the weight of such other compounds is ignored in the calculation of the purity of the preparation.

As used herein, the terms "modulate" or "affect" mean to either increase or decrease. As used herein, the terms "increase" and "decrease" mean, respectively, statistically significantly increase (i.e., $p<0.1$) and statistically significantly decrease (i.e., $p<0.1$).

As used herein, the term "contacted" as in the phrase "A is contacted with B," means that A and B are brought into sufficient physical proximity to interact at the molecular level, as by mixing A and B together in a solution, or pouring a solution of A over B on a substrate. As used herein, the phrase "A is contacted with B" is intended to be equivalent to "B is contacted with A" and is not intended to imply that either element is fixed relative to the other, or that either element is moved relative to the other.

Numerical Ranges. As used herein, the recitation of a numerical range for a variable is intended to convey that the invention may be practiced with the variable equal to any of the values within that range. Thus, for a variable which is inherently discrete, the variable can equal each integer value of the numerical range, including the end-points of the range. Similarly, for a variable which is inherently continuous, the variable can equal each real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value ≤2 for variables which are inherently continuous.

Or. As used herein, unless specifically indicated otherwise, the word "or" is used in the "inclusive" sense of "and/or" and not the "exclusive" sense of "either/or."

General Considerations.

The present invention depends, in part, upon the identification, isolation and characterization of a cation channel protein which is expressed in sperm cells, but not in other tissues tested, and which plays a significant role in the motility of sperm and then ability to fertilize ova. The protein has been designated CatSper2 to indicate that it is the second Cation channel which is Sperm-specific to be identified. The CatSper2 channel protein is present on the flagellum and, therefore, plays a role in sperm cell motility. Therefore, inhibitors of the activity of the CatSper2 protein can be used as sperm-inhibiting contraceptives by men and/or women to cause temporary, reversible infertility.

The predicted CatSper2 ORF encodes a protein with six transmembrane segments (FIG. 1(A), SEQ ID NO: 1, SEQ ID NO: 3 and SEQ ID NO: 5). The sequences show similarities to the voltage-gated calcium channel family ($Ca_v$), and are most similar to CatSper1 another sperm cell-specific putative cation channel recently found to be important for motility and normal fertilization (FIG. 1(B)) (Ren et al. (2001), supra). Thus, CatSper2 and CatSper1 define a new family of ion channels (Saier (2000), *J. Membr. Biol.* 175:165-80; Catterall (2000), *Annu. Rev. Cell Dev. Biol.* 16:521-55). The features of this family include the presence of a single transmembrane region with six membrane spanning segments and an apparent S4 voltage sensor, characteristics shared by the $K_v$ and HCN channels, combined with a predicted calcium-selective pore region and an overall sequence similarity of the transmembrane region with the four transmembrane repeats in the voltage-gated calcium and sodium channels.

CatSper2 Nucleic Acids.

In one aspect, the present invention provides nucleic acid molecules, or nucleic acid analogs, encoding the CatSper2 proteins, or useful fragments thereof. Two cDNAs of the human CatSper2 gene have been identified and are apparent splice variants of each other. These sequences are disclosed as SEQ ID NO:1 and SEQ ID NO: 3, and as Genbank Accession No. AF411817 and Genbank Accession No. AF411819, respectively. The full-length cDNA sequence of a murine homolog is disclosed as SEQ ID NO: 5 and as Genbank Accession No. AF411816.

Nucleic acid molecules of the invention can be DNA or RNA molecules, or hybrid DNA-RNA molecules. The nucleic acid analogs of the invention can be any of those known in the art, such as peptide nucleic acids, analogs including modified bases (e.g., 2'-halogeno-2'-deoxynucleosides) and/or analogs including modified internucleoside linkages (e.g., phosphorothioate linkages), which are useful in applications such as in vitro translation or antisense technologies. The nucleic acids can be sense molecules corresponding to all or a portion of a CatSper2 gene sequence, or can be antisense molecules which are complementary to all or a portion of a CatSper2 gene sequence. The nucleic acids can be derived from or correspond to genomic DNA or cDNA, or can be synthetic molecules based upon a CatSper2 protein sequence and the genetic code (e.g., synthetic nucleic acids which reflect the codon usage preferences in the host cells used in an expression system).

In some embodiments, the CatSper2 nucleic acids comprise the entire coding region of a CatSper2 gene (e.g., SEQ ID NO: 1, SEQ ID NO: 3 or SEQ ID NO: 5). Such nucleic acids can be used to produce genetic constructs for transformation of cells, or for in vitro transcription and translation systems. Such nucleic acids can also be used as probes in hybridization assays to detect CatSper2 sequences in samples of other nucleic acids.

In other embodiments, subsets of the CatSper2 nucleic acid sequences are provided for use as primers for nucleic acid amplification reactions, as probes in hybridization assays to detect CatSper2 sequences in samples of other nucleic acids, or as probes to distinguish normal or wild-type sequences from abnormal or mutant sequences. In these embodiments, the nucleic acids of the invention comprise at least 10, 12, 14, 16 or 18 consecutive nucleotides selected from a CatSper2 sequence such as SEQ ID NO: 1. Depending upon the nature of the application, it can be preferable to choose CatSper2 sequences which will have unique targets, or which are expected to have unique targets, within a sample being probed or amplified. Thus, for example, sequences which are longer and sequences which do not include frequently repeated elements (for example, polyadenylation signals) are more likely to be uniquely represented within any given sample. For purposes of choosing primers for amplification reactions, sequences of at least 15 nucleotides, and typically 18-25 nucleotides, are used.

In certain embodiments, nucleic acids are provided which encode structural domains of a CatSper2 protein, or which encode fragments of the protein which can serve as epitopes for the generation of antibodies. Thus for example, useful nucleic acids include those encoding the transmembrane domains of the CatSper2 proteins (i.e., approximately residues 104-126, 146-166, 176-195, 206228, 241-262, and 316-340 of SEQ ID NO: 2, approximately residues 104-126, 146-166, 176-195, 206-228, 241-262, and 316-340 of SEQ ID NO: 4, approximately residues 102424, E14464, 17-393, 204-227, 239-260, and 314-338 of SEQ ID NO: 6, and allelic variants and homologs thereof), encoding the extracellular loops between transmembrane domains (i.e., 127-145, 196-205, and 263-315 of SEQ ID NO: 2, 127-145, 196-205, and 265-315 of SEQ ID NO: 4, 125-143, 194-203, and 261-313 of SEQ ID NO: 6, and allelic variants and homologs thereof), or encoding the pore region (i.e., from approximately residue 280 to approximately residue 303 of SEQ ID NO: 2, from approximately residue 280 to approximately residue 303 of SEQ ID NO: 4, from approximately residue 278 to approximately residue 301 of SEQ ID NO: 6, and allelic variants and homologs thereof). Other useful nucleic acids include those encoding potential epitopes of the CatSper2 proteins, as identified by standard sequence analysis techniques described below. Thus, for example, useful nucleic acids include those encoding the following human CatSper2 sequences: residues 266-275, residues 386-400, residues 447-458, and residues 482-494 of SEQ ID NO:

2, residues 66-99, residues 266-275, and residues 394-414 of SEQ ID NO: 4, and residues 64-89, residues 262-275, and residues 562-588 of SEQ ID NO: 6. Other useful epitopes include allelic and non-human mammalian homologs of these epitopes.

In certain embodiments, nucleic acids are provided which encode polypeptides have at least 80%, 85%, 90% or 95% amino acid sequence identity with at least a structural domain of a CatSper2 protein. Thus, in some embodiments, a nucleic acid is provided which encodes a polypeptide having at least 80%, 85%, 90% or 95% amino acid sequence identity with a transmembrane domain of a CatSper2 protein (e.g., approximately residues 104-426, 146-166, 176-195, 206-228, 241-262, and 316-340 of SEQ ID NO: 2; approximately residues 104-126, 146-166, 176-195, 206-228, 241-262, and 316-340 of SEQ ID NO: 4; approximately residues 102-124, 144-164, 174-193, 204-227, 239-260, and 314-338 of SEQ ID NO: 6; and allelic variants and homologs thereof), an extracellular loop between transmembrane domains (e.g., approximately residues 127-145, 196-205, and 263-315 of SEQ ID NO: 2; approximately residues 127-145, 196-205, and 265-315 of SEQ ID NO: 4, approximately residues 125-143, 194-203, and 261-313 of SEQ ID NO: 6; and allelic variants and homologs thereof), or a pore region (e.g., approximately residues 280-303 of SEQ ID NO: 2; approximately residues 280-303 of SEQ ID NO: 4; approximately residues 278-301 of SEQ ID NO: 6; and allelic variants and homologs thereof). In some embodiments, nucleic acids are provided encoding a polypeptide having at least 80%, 85%, 90% or 95% amino acid sequence identify with a CatSper2 protein and having CatSper2 activity. The ability of a protein to exhibit CatSper2 activity can be measured by its ability to complement a CatSper2−/− mutant (e.g., a CatSper2 knock-out mutant) and restore a normal or CatSper2+/+ phenotype (e.g., to restore sperm motility) in a cell otherwise capable of expressing CatSper2 activity (e.g., a sperm cell from the CatSper2−/− mutant).

In other embodiments, isolated nucleic acids are provided which include a nucleotide sequence that hybridizes to at least a portion of a CatSper2 coding sequence (e.g., SEQ ID NO: 1 or SEQ ID NO: 3 or SEQ ID NO: 5) under stringent hybridization conditions. Such conditions include hybridizations employing a wash step of 1.0×SSC at 65° C., and equivalents thereof. More stringent conditions can include wash steps of 0.5×SSC, 0.2×SSC, or even 0.1×SSC. Other equivalently stringent conditions are well known in the art. See, e.g., Ausubel et al., eds. (1989), *Current Protocols in Molecular Biology*, Vol. 1 John Wiley & Sons, Inc., New York. In some embodiments, the nucleic acid encodes a polypeptide having CatSper2 activity.

In another aspect, the invention provides nucleic acids, either isolated or existing within cells, in which a nucleotide sequence encoding a polypeptide having CatSper2 activity is operably joined to a heterologous regulatory region such that the CatSper2 sequence is expressed. Thus, in certain embodiments, a heterologous regulatory region can be inserted into a chromosome such that it is operably joined to an endogenous CatSper2 sequence. In some embodiments, the polypeptide has sat least 80%, 85%, 90% or 95% amino acid sequence identity with an amino acid sequence of SEQ ID NO: 2 or SEQ ID NO: 4 or SEQ ID NO: 6. In other embodiments, the nucleic acid encoding the polypeptide hybridizes to at least a portion of a nucleic acid of SEQ ID NO: 1 or SEQ ID NO: 2 or SEQ ID NO: 5 under conditions including a wash step of 1.0×SSC at 65° C., 0.5×SSC, 0.2×SSC, or 0.1×SSC.

In certain embodiments, the nucleic acids of the invention encode polypeptides including a CatSper2 sequence of at least 50 amino acid residues in length, or at least 100, 200 or 300 amino acid residues in length. These polypeptides can include a CatSper2 sequence which includes at least one transmembrane domain, at least one extracellular loop domain, at least a pore region, or combinations thereof. In some embodiments, the polypeptide has CatSper2 activity. Such activity can include induction of ion current; mediation of cAMP-induced $Ca^{2+}$ influx; restoration of sperm motility when expressed in CatSper2−/− sperm; and/or restoration of the ability to fertilize eggs when expressed in CatSper2−/− sperm.

In another aspect, the invention provides kits for detecting at least a portion of a CatSper2 nucleic acid (i.e., CatSper2 genomic DNA, mRNA, cDNA or amplification products thereof). The kits include an isolated nucleic acid of the invention as a probe and means for demoting the probe. The means for detecting the probe can be a detectable label bound to the probe or a secondary nucleic acid probe for detecting the first probe (e.g., labeled secondary nucleic acid which specifically hybridizes to the isolated nucleic acid.).

Genetic Constructs.

In another aspect, the present invention provides genetic constructs comprising sequences selected from CatSper2 genes. In certain embodiments, the CatSper2 gene sequences are selected from the coding region of the CatSper2 gene, and in other embodiments, the CatSper2 gene sequences can be chosen from the CatSper2 regulatory regions extending approximately 1,000 bases 5' of the transcription initiation codon, and extending approximately 1,000 bases 3' of the termination codon.

In one series of embodiments, CatSper2 coding sequences (e.g., the entire coding region, sequences encoding structural domains, sequences encoding potential epitopes, or sequences encoding useful primers or probes) are operably joined to an endogenous or exogenous regulatory region to form an expression construct. Useful regulatory regions for these purposes include the endogenous CatSper2 regulatory region, constitutive promoter sequences (e.g., CMV, SV40, EP2), and inducible promoter sequences (e.g., lacZ, tet). Many useful vector systems are commercially available. For example, useful bacterial vectors include, but are not limited to, pQE70, pQE60, pQE-9 (Qiagen, Valencia, Calif.), pBluescript II™ (Stratagene, La Jolla, Calif.), and pTRC99a, pKK223-3, pDR540 and pRIT2T (Pharmacia, Piscataway, N.J.), pTrc (Amann et al. (1988), *Gene* 69:301-315) and pET 11d (Studier et al. (1990), *Methods in Enzymol.* 185:60-89). Examples of vectors for expression in yeast include pYepSec1 (Baldari et al. (1987), *EMBO J.* 6:229-234), pMFa (Kurjan et al. (1982), *Cell* 30:933-943), pJRY88 (Schultz et al. (1987), *Gene* 54:113-123), and pYES2 (Invitrogen Corporation, San Diego, Calif.). The CatSper2 proteins can also be expressed to insect cells (e.g., Sf9 cells) using, for example, baculovirus expression vectors including, but not limited to, pAc vectors (Smith et al. (1983), *Mol. Cell Biol.* 3:2156-2165) and pVL vectors (Lucklow et al. (1989), *Virology* 170:31-39). Examples of mammalian expression vectors include, but are not limited to, pCDM8 (Seed (1987), *Nature* 329:840) and pMT2PC (Kaufman et al. (1987), *EMBO J.* 6:187-195). Other useful eukaryotic vectors include, but are not limited to, pXT1, pSG5 (Stratagene, La Jolla, Calif.), and pSVK3, pBPV, pMSG, and PSVLSV40 (Pharmacia, Piscataway, N.J.). Thus, one of ordinary skill in the art can choose a vector system appropriate to the host cell to be transformed.

In other embodiments, the vectors comprise defective or partial CatSper2 sequences in a "knock-out" vector. Such vectors are well-known in the art and can be used to produce a transgenic organism in which an endogenous gene is "knocked-out" by recombination with a partially homologous exogenous sequence which introduces a mutation within the endogenous sequence. Typically, the vector is directed at an endogenous target sequence which can be all or part of a gene of interest. The vector includes 5' and 3' flanking sequences which are homologous to the 5' and 3' ends of the target. Between the 5' and 3' flanking sequences is the sequence including the mutation. The mutation can be a termination mutation, frame-shift mutation, large deletion, or even the introduction of a new coding sequence which serves both to disrupt the endogenous gene and to act as a marker to identify successful homologous recombinants. Knock-out vectors are further discussed below.

In another series of embodiments, the CatSper2 coding sequences can be joined to regulatory regions and exogenous coding sequences to form a genetic construct or fusion vector which encodes a fusion protein. In some embodiments, the CatSper2 coding sequences can be joined to exogenous coding sequences that confer new and useful properties to the fusion protein. For example, fusion vectors and fusion proteins can be useful to increase the expression of the CatSper2 protein, to increase the solubility of the CatSper2 protein, or to aid in the purification of the CatSper2 protein (e.g., by providing a ligand sequence for affinity purification). A proteolytic cleavage site can be introduced at the junction of the CatSper2 and the non-CatSper2 protein sequences so that the CatSper2 protein can easily be separated from the fusion moiety. Typical fusion expression vectors include pGEX (Smith et al. (1988), *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

In another series of embodiments, genetic constructs are produced in which the coding region from a reporter gene is operably joined to the regulatory region of a CatSper2 gene. Such genetic constructs are useful in assays to identify or characterize compounds that enhance or repress CatSper2 gene expression by enhancing or repressing transcription of the CatSper2 gene. A wide variety of suitable reporter genes are known to those of skill in the art, and are commercially available. Examples include, but are not limited to, the lacZ, luciferase and green fluorescent protein genes.

Useful CatSper2 regulatory elements include sequences having at least 80% nucleotide identity to at least 100-1,000, 200-800 or 300-700 consecutive nucleotides selected from the 1,000 nucleotides immediately 5' to the CatSper2 transcription initiation site. Useful regulatory elements retain the ability to promote transcription of a coding sequence operably joined to the element in a mammalian cell in which a CatSper2 gene is expressed. In particular, useful regulatory elements retain the ability to promote transcription in cells in which the CatSper2 gene from which the element was derived is expressed, or in which a homolog of that CatSper2 gene is expressed.

Transformed Cell Lines.

In another aspect, the present invention provides cell lines transformed with the nucleic acid molecules of the invention. Such cell lines can simply propagate these nucleic acids (e.g., when transformed with cloning vectors) or can express the polypeptides encoded by these nucleic acids (e.g., when transformed with expression vectors). Such transformed cell lines can be used to produce the CatSper2 proteins and CatSper2 fragments of the invention, or can be used in assays to screen for compounds that enhance, repress, agonize, or antagonize CatSper2 expression or activity.

The transformed cells can be produced by introducing into a cell an exogenous nucleic acid or nucleic acid analog which replicates within that cell, that encodes a polypeptide sequence which is expressed in that cell, and/or that is integrated into the genome of that cell so as to affect the expression of a genetic focus. The transformation can be achieved by any of the standard methods referred to in the art as transformation, transfection, transduction, electroporation, ballistic injection, and the like. The method of transformation is chosen to be suitable to the type of cells being transformed and the nature of the genetic construct being introduced into the cells.

Useful cell lines for transformation include bacterial cells (e.g., *Escherichia coli*), yeast cells (e.g., *Saccharomyces cerevisiae*), insect cells (e.g., *Drosophila melanogaster* Schneider cells), nematode cells (e.g., *Caenorhabditis elegans*), amphibian cells (e.g., *Xenopus oocytes*), rodent cells (e.g., *Mus musculus* (e.g., murine 3T3 fibroblasts). *Rattus rattus*, Chinese Hamster Ovary cells (e.g., CHO-K1)), and human cells (e.g., human skin fibroblasts, human embryonic kidney cells (e.g., HEK-293 cells), COS cells). Although these and many other types of cells can be transformed for purposes of producing the CatSper2 protein, preliminary studies have found that transformation of CHO-K1 and HEK-293 cells does not result in detectable CatSper2 activity as determined by patch-clamp measurements of channel currents. These latter cells appear to lack co-factors or accessory proteins present in sperm which are necessary to CatSper2 activity, structural attributes of sperm which are necessary for functional channel organization, or a necessary CatSper2 post-translational processing or localization mechanism. Yeast two hybrid approaches and co-immunoprecipitation approaches can be used to screen libraries to identify CatSper2 accessory, associating or interacting proteins, including modulators of CatSper2 activity.

Appropriate cells can be transformed with any of the above-described genetic constructs in order to produce CatSper2 proteins, including fragments of CatSper2 proteins, fusion proteins of CatSper2 proteins, or marker proteins under the control of a CatSper2 regulatory region.

The cells can be transformed according to any method known in the art appropriate to the cell type being transformed. Appropriate methods include those described generally in, e.g., Sambrook et al. (1989), *Molecular Cloning; A Laboratory Manual*, Cold Spring Harbor Laboratories, New York; and Davis et al. (1986), *Basic Methods in Molecular Biology*, Elsevier. Particular methods include calcium phosphate co-precipitation (Graham et al. (1973), *Virol.* 52:456-467), direct microinjection into cultured cells (Capecchi (1980), *Cell* 22:479-488), electroporation (Shigekawa et al. (1988), *BioTechniques* 6:742-751), liposome-mediated gene transfer (Mannino et al. (1988), *BioTechniques* 6:682-690), lipid-mediated transduction (Felgner et al. (1987), *Proc. Natl. Acad. Sci. USA* 84:7413-7417), and nucleic acid delivery using high-velocity microprojectiles (Klein et al. (1987). *Nature* 327:70-73).

Transgenic Animals.

The present invention also provides for the production of transgenic non-human animal models in which wild type, allelic variant, chimeric, or antisense CatSper2 sequences are expressed, or in which CatSper2 sequences have been inactivated or deleted (e.g., "knock-out" constructs) or replaced with reporter or marker genes (e.g., "knock-in reporter" constructs). The CatSper2 sequences can be conspecific to the transgenic animal (e.g., murine sequences in a transgenic mouse) or transpecific to the transgenic animal (e.g. human sequence in a transgenic mouse). In such a transgenic animal, the transgenic sequences can be expressed inducibly, constitutively or ectopically. Expression can be tissue-specific or organism-wide. Engineered expression of CatSper2 sequences in tissues and cells not normally containing CatSper2 gene products can cause novel alterations of cation flux and lead to novel cell or tissue phenotypes. Ectopic or altered levels of expression of CatSper2 sequences can alter cell, tissue and/or developmental phenotypes. Transgenic animals are useful as models of disorders arising from defects in CatSper2 activity.

Transgenic animals are also useful for screening compounds for their effects on CatSper2 activity. Transgenic animals transformed with reporter constructs can be used to measure the transcriptional effects of small molecules or drugs on physical perturbations on the expression of CatSper2 genes and proteins in vivo. The transgenic animals of the invention, can be used to screen such compounds for therapeutic utility.

Animal species suitable for use in the animal models of the present invention include, but are not limited to, rats, mice, hamsters, guinea pigs, rabbits, dogs, cats, goats, sheep, pigs, and non-human primates (e.g., Rhesus monkeys, chimpanzees). For initial studies, transgenic rodents (e.g., mice) can be used due to their relative ease of maintenance and shorter life spans. Transgenic non-human primates can be used for longer term studies due to their greater similarity to humans.

Using the nucleic acids disclosed and otherwise enabled herein, there are several embodiments of the creation of a transgenic animal. Thus, useful animal models include; (1) animals in which sequences encoding at least a functional fragment of a CatSper2 gene has been recombinantly introduced into the genome of the animal as an additional gene, under the regulation of either as exogenous or an endogenous promoter element, and as either a minigene (i.e., a genetic construct of the CatSper2 gene based on cDNA with introns removed) or a huge genomic fragment; (2) animals in which sequences encoding at least a functional fragment of a CatSper2 gene have beets recombinantly substituted for one or both copies of the animal's endogenous CatSper2 gene by homologous recombination or gene targeting; (3) animals in which one or both copies of one of the animal's homologous CatSper2 genes have been recombinantly "humanized" by the partial substitution of sequences encoding the human homolog by homologous recombination or gene targeting; (4) animals in which sequences encoding a reporter gene have replaced the endogenous CatSper2 gene by homologous recombination; (5) and "knock-out" animals in which one or both copies of the animal's CatSper2 sequences have been partially or completely inactivated by the insertion, deletion or substitution of one or more nucleotides by homologous recombination. These and other transgenic animals of the invention are useful as models of infertility or other disorders arising from defects in the CatSper2 gene and/or protein. These animals are also useful for screening compounds for their effects on the CatSper2 gene and/or protein.

To produce an animal model (e.g., a transgenic mouse), a wild type or allelic variant CatSper2 sequence or a wild type or allelic variant of a recombinant nucleic acid encoding at least a functional fragment of a CatSper2 protein can be inserted into a germ line or stem cell using standard techniques of oocyte or embryonic stem cell microinjection, or other methods of transformation of such cells. Alternatively, other cells from an adult organism can be employed. Animals produced by these or similar processes are referred to as transgenic. Similarly, if it is desired to inactivate or replace an endogenous CatSper2 sequence, homologous recombination using *oocytes*, embryonic stem or other cells can be employed. Animals produced by these or similar processes are referred to as "knock-out" (inactivation) or "knock-in" (replacement) models.

For oocyte injection, one or more copies of the recombinant DNA constructs of the present invention can be inserted into the pronucleus of a just-fertilized oocyte. This oocyte is then reimplanted into a pseudo-pregnant foster mother. The live born animals are screened for integrants using standard DNA/mRNA analysis (e.g., from the tail veins of offspring mice) for the presence of the inserted recombinant transgene sequences. The transgene can be either a complete genomic sequence introduced into a host as part of a yeast artificial chromosome (YAC), bacterial artificial chromosome (BAC), or other chromosome DNA fragment; as a cDNA with either the endogenous promoter or a heterologous promoter; or as a minigene containing all of the coding regions and other elements found to be necessary for optimum expression.

To create a transgene, the target sequence of interest (e.g., a wild type or allelic variant of a CatSper2 sequence) is typically ligated into a cloning site located downstream of a promoter element which will regulate the expression of RNA from the sequence. Downstream of the coding sequence, there is typically a polyadenylation sequence. An alternative approach to creating a transgene is to use an exogenous promoter and regulatory sequences to drive expression of the transgene. Finally, it is possible to create transgenes using large genomic DNA fragments such as YACs which contain the entire desired gene as well as its appropriate regulatory sequences.

Animal models can be created by targeting endogenous CatSper2 sequences for homologous recombination. These targeting events can have the effect of removing an endogenous sequence (knock-out) or altering the endogenous sequence to create an amino acid change associated with human disease or an otherwise abnormal sequence (e.g., a sequence which is more like the human sequence than the original animal sequence) (knock-in animal models). A large number of vectors are available to accomplish such changes, and appropriate sources of genomic DNA for moose and other animals are commercially available (e.g., GenomeSystems Inc., St. Louis, Mo.).

The typical feature of these targeting vector constructs is that 2 to 4 kb of genomic DNA is ligated 5' to a selectable marker (e.g., a bacterial neomycin resistance gene under its own promoter element termed a "neomycin cassette"). A second DNA fragment from the gene of interest is then ligated downstream of the neomycin cassette but upstream of a second selectable marker (e.g., thymidine kinase). The DNA fragments are chosen such that mutant sequences can be introduced into the germ line of the targeted animal by homologous replacement of the endogenous sequences by either one of site sequences included in the vector. Alternatively, the sequences can be chosen to cause deletion of sequences that would normally reside between the left and right arms of the vector surrounding the neomycin cassette. The former is known as a knock-in, the latter is known as a knock-out.

Early embryos can also be infected to insert the recombinant DNA constructs of the invention. In this method, the transgene (e.g., a wild type or allelic variant of a CatSper2 sequence) is inserted into a viral or retroviral vector which is used to directly infect embryos (e.g., mouse or non-human primate embryos) during the early stages of development to generate partially transgenic animals. Some of the partially transgenic animals will bear the transgenes in germ line cells and can be bred to produce fully transgenic animals.

Alternatively, homologous recombination using a population of stem cells allows for the screening of the population for successful transformants. Once identified, these can be injected into blastocysts, and a proportion of the resulting animals will show germ line transmission of the transgene. These partially transgenic animals can be bred to produce fully transgenic animals.

Techniques of generating transgenic animals, as well as techniques for homologous recombination or gene targeting, are now widely accepted and practiced. A laboratory manual on the manipulation of the mouse embryo, for example, is available which details standard laboratory techniques for the production of transgenic mice (Hogan et al. (1986), *Manipulating the Mouse Embryo*, Cold Spring Harbor Laboratory Press, Cold Spring Harbor, N.Y.).

CatSper2 Proteins and Polypeptides.

In another aspect, the present invention provides substantially pure preparations of CatSper2 proteins. The proteins can be isolated from sperm cells, using standard techniques such as immunoaffinity purification with the antibodies of the invention (see below), or can be isolated from the transformed cells of the invention, in which they can be expressed at higher levels and, optionally, as fusion proteins which are more easily isolated and/or purified.

In some embodiments, the CatSper2 proteins comprise the entire translated sequence of the CatSper2 coding region. Examples of such full-length CatSper2 proteins include the human CatSper2 proteins disclosed as SEQ ID NO: 2 and SEQ ID NO: 4 and the mouse homolog disclosed as SEQ ID NO: 6, as well as allelic and non-human homologs of CatSper2 proteins, and functional equivalents thereof.

In other embodiments, the CatSper2 proteins are CatSper2 fragments. Such fragments include the structural domains of the CatSper2 proteins, including the transmembrane, loop and pore-forming regions of the proteins. Useful structural domains include the transmembrane domains of the human CatSper2 protein (i.e., approximately residues 104-126, 146-166, 179-195, 206-228, 241-262, and 316-340 of SEQ ID NO: 2; approximately residues 104-126, 146-166, 176-195, 206-228, 241-262, and 316-340 of SEQ ID NO: 4; approximately residues 102-124, 144-164, 174-193, 204-227, 239-260, and 314-338 of SEQ ID NO: 6), the extracellular loops between transmembrane domains (i.e., approximately residues 127-145, 196-205, and 263-315 of SEQ ID NO: 2; approximately residues 127-145, 196-205, and 265-315 of SEQ ID NO: 4; approximately residues 125-443, 194-203, and 261-313 of SEQ ID NO: 6), and the pore region (i.e., approximately residues 280-303 of SEQ ID NO: 2; approximately residues 260-303 of SEQ ID NO: 4, approximately residues 278-301 of SEQ ID NO: 6), as well as allelic variants and non-human homologs thereof. Other CatSper2 fragments include potentially useful epitopes of the CatSper2 proteins, as identified by standard sequence analysis techniques. Thus, for example, useful CatSper2 fragments include the following human CatSper2 sequences: residues 266-275, 386-400, 447-458 and 482-494 of SEQ ID NO: 2; residues 66-99, 266-275 and 394-414 of SEQ ID NO: 4; and residues 64-89, 262-275 and 562-588 of SEQ ID NO: 6.

In certain embodiments, polypeptides are provided having at least 80%, 85%, 90% or 95% amino acid sequence identity with at least a structural domain of a CatSper2 protein. Thus, in some embodiments, a polypeptide is provided having at least 80%, 8593, 90% or 95% amino acid sequence identity with a transmembrane domain of a CatSper2 protein (e.g., approximately residues 104-126, 146-166, 176-195, 206-228, 241-262, and 316-340 of SEQ ID NO: 2; approximately residues 104-126, 146-166, 176-195, 206-228, 241-262, and 316-340 of SEQ ID NO: 4; approximately residues 102-124, 144-164, 174-193, 204-227, 239-260, and 314-338 of SEQ ID NO: 6, and allelic variants and homologs thereof), an extracellular loop between transmembrane domains (e.g., approximately residues 127-145, 196-205, and 263-315 of SEQ ID NO: 2; approximately residues 127-145, 196-205, and 265-315 of SEQ ID NO: 4; approximately residues 125-143, 194-203, and 261-313 of SEQ ID NO: 6, and allelic variants and homologs thereof), or a pore region (e.g., approximately residues 280-303 of SEQ ID NO: 2, approximately residues 280-303 of SEQ ID NO: 4, approximately residues 278-301 of SEQ ID NO: 6, and allelic variants and homologs thereof). In some embodiments, polypeptides are provided having at least 80%, 85%, 90% or 95% amino acid sequence identity with a CatSper2 protein and having CatSper2 activity. The ability of a protein to exhibit CatSper2 activity can be measured by its ability to complement a CatSper2−/− mutant (e.g., a CatSper2 knock-out mutant) and restore a normal or CatSper2+/+ phenotype (e.g., to restore sperm motility) in a cell otherwise capable of expressing CatSper2 activity (e.g., a sperm cell from the CatSper2−/− mutant).

In certain embodiments, the polypeptides of the invention include a CatSper2 sequence of at least 50 amino acid residues in length, or at least 100, 200 or 300 amino acid residues in length. These polypeptides can include a CatSper2 sequence which includes at least one transmembrane domain, at least one extracellular loop domain, at least a pore region, or combinations thereof. In some embodiments, the polypeptide has CatSper2 activity. Such activity can include the induction of ion currents; when expressed in a cell (e.g., an oocyte); mediation of cAMP-induced $Ca^{2+}$ influx; restoration of sperm motility when expressed in CatSper2−/− sperm; and/or restoration of the ability to penetrate eggs when expressed in CatSper2−/− sperm.

Antibodies Against CatSper2 Proteins and Polypeptides.

In another aspect, the present invention provides substantially pure preparations of antibodies against the CatSper2 proteins, and methods of making such antibodies. The antibodies can be polyclonal or monoclonal, and can be made by methods web known in the art. In particular, the invention provides antibodies raised against CatSper2 epitopes having high predicted antigenicity, which therefore will selectively bind to and, thereby, isolate or identify wild type and/or variant forms of the CatSper2 proteins.

The antibodies can be raised against the full-length CatSper2 proteins, against fragments of the CatSper2 proteins, or using any CatSper2 epitopes which are characteristic of the proteins and which substantially distinguish them from other proteins. In certain embodiments, the antibodies are raised against CatSper2 epitopes including, but not limited to, residues 266-275, 386-400, 447-458 and 482-494 of SEQ ID NO: 2; residues 60-99, 266-275 and 304-414 of SEQ ID NO: 4; and residues 64-89, 262-275 and 562-588 of SEQ ID NO: 6. Other useful epitopes include allelic and non-human homologs of these epitopes. Epitopes having a high predicted antigenicity were identified by prediction of hydrophobicity, surface probability and antigenic index using standard programs, including GCG and MacVector (Genetics Computer Group, University of Wisconsin Biotechnology Center, Madison, Wis.; Accelrys Inc., San Diego, Calif.). See also, Jameson and Wolf (1988), *Comput. Appl. Biosci.* 4:181-186.

CatSper2 immnnogen preparations can be produced from crude extracts (e.g., microsomal fractions of cells expressing the proteins), from proteins or peptides substantially purified from cells which naturally or recombinantly express them or, for small immunogens, by chemical peptide synthesis. The CatSper2 immunogens can also be in the form of a fusion protein in which the non-CatSper2 portion is chosen for its adjuvant properties and/or its ability to facilitate purification (e.g., polyhistidine).

The antibodies of the invention can be polyclonal or monoclonal, or can be antibody fragments, including Fab fragments, $F(ab')_2$ fragments, Fv fragments, and single chain Fv fragments (scFv). In addition, after identifying useful antibodies by the method of the invention, recombinant antibodies can be generated, including any of the antibody fragments listed above, as well as chimeric and/or humanized antibodies based upon non-human antibodies to the CatSper2 proteins. In light of the present disclosure of CatSper2 proteins, as well as the characterization of other CatSper2 proteins enabled herein, one of ordinary skill in the art can produce the above-described antibodies by any of a variety of standard means. For an overview of antibody techniques, see *Antibody Engineering*, 2nd Ed., Borrebaek, ed., Oxford University Press, Oxford (1995).

As a general matter, monoclonal anti-CatSper2 antibodies can be produced by first Injecting a mouse, rabbit, goat or other suitable animal with a CatSper2 immnnogen in a suitable carrier or diluent. Carrier proteins or adjuvants can be utilized, and booster injections (e.g., bi- or tri-weekly over 8-10 weeks) can be employed as necessary. After allowing for development of a humoral response, the animals are sacrificed and their spleens are removed and resuspended in an appropriate buffer (e.g., phosphate buffered saline). The spleen cells serve as a source of lymphocytes, some of which will produce antibodies of the appropriate specificity. These cells are then fused with an immortalized cell line (e.g., a myeloma), and the products of the fusion are plated into tissue culture wells in the presence of a selective agent (e.g., HAT). The wells are serially screened and replated, selecting cells making a useful antibody each time. Typically, several screening and replating procedures are carried out until the wells contain single clones which are positive for antibody production. Monoclonal antibodies produced by such clones can be purified by standard methods such as affinity chromatography using Protein A Sepharose, by ion-exchange chromatography, or by variations and combinations of these techniques.

The antibodies of the invention can be used in a variety of applications. For example, antibodies can be used in a purification process (e.g., immunoaffinity purification) for CatSper2 proteins, in assays to detect the presence or level of CatSper2 proteins (e.g., in a diagnostic test for a CatSper2-related disorder), or in assays to measure the presence or level of CatSper2 expression in transformed cells (e.g., in assays for regulators of CatSper2 expression, in Western blotting to identify cells expressing CatSper2 proteins, or in immunocytochemistry or immunofluorescence techniques to establish the cellular or extracellular location of CatSper2 proteins).

The antibodies of the invention can be bound to or conjugated with other compounds or materials for diagnostic and/or therapeutic uses. For example, they can be coupled to labels such as radionuclides, fluorescent compounds (e.g., rhodamine), or enzymes for imaging or therapy. The labels can be bound to the antibodies covalently or non-covalently.

In another aspect, the invention provides kits for detecting at least an epitope of a CatSper2 protein. The kits include an anti-CatSper2 antibody and a means for detecting the antibody. The means for detecting the antibody can be a detectable label bound to the antibody or secondary antibodies for defecting the anti-CatSper2 antibodies (e.g., a labeled goat anti-rabbit-Ig antibody as a secondary antibody for detecting a rabbit anti-CatSper2 antibody).

Assays for Modulators of CatSper2 Expression or Activity.

In another aspect, the present invention provides assays for modulators of CatSper2 expression or activity. The modulators can affect the transcription, translation, post-translational processing, localization, or activity of a CatSper2 gene and/or protein.

Thus, in one series of embodiments, the transformed cells of the invention are contacted with a candidate compound, and the effect of the compound on the expression or activity of CatSper2 is determined. As a general matter, the assays require contacting a candidate compound with a cell expressing a CatSper2 protein and measuring an indicator of CatSper2 activity in the cell. The indicator can be an indicator of transcription (e.g., mRNA levels), translation (e.g., protein levels), post-translational; processing (e.g., specific glycosylation), localization (e.g., immunohistochemistry), or activity (e.g., sodium or other monovalent ion flax; calcium or other divalent ion flux). The indicator measurement is then compared to a reference level to determine whether the candidate compound caused an increase or decrease in the indicator. The reference level can be extrinsic (e.g., a predetermined baseline level) or intrinsic (e.g., a measurement of the same cell prior to contact with the candidate compound). If an increase or decrease is significant (based on a single reading or on multiple readings from one or more cells), the candidate compound is identified as a potential modulator of CatSper2 activity. Assays for changes in CatSper2 activity can include any of those used routinely in the art for other genes. For example, changes in the presence or levels of CatSper2 mRNA or protein can be detected to identify enhancers or repressors of CatSper2 expression. Alternatively, when using a reporter gene construct of the invention, the biochemical or phenotypic change characteristic of the reporter can be used as an indication that the candidate compound enhances or represses reporter gene expression. In other embodiments, changes in the activity of the CatSper2 protein can be detected by measuring, for example, the flux of cations mediated by the CatSper2 protein, or by measuring whole cell or channel currents. Measurements of ion fluxes can be facilitated by the use of chromophores which change color depending upon the concentration of specific ions. The effects of candidate compounds on mature sperm cells can be tested to confirm or validate results obtained in the transformed cells of the invention.

Compounds which bind to CatSper2 are candidates for modulating CatSper2 activity. Thus, in another series of embodiments, libraries of compounds can be screened to identify candidates for modulating CatSper2 activity by contacting candidate compounds with a CatSper2 protein, or at least a structural domain of a CatSper2 protein, to identify compounds that bind to CatSper2. CatSper2 structural domains which can be used in these methods include transmembrane domains, and particularly extracellular loops and pore regions. In such methods, the CatSper2 protein or CatSper2 structural domain can be immobilized (e.g., on a column or microparticle) and a solution of the candidate compound can be contacted with the CatSper2 moiety, or the candidate compound can be immobilized (e.g., on a column of microparticle) and a solution of the CatSper1 moiety can be contacted with the candidate compound. Alternatively, in some embodiments, neither the candidate compound nor the CatSper2 moiety is immobilized but, rather, both are in solution and binding is detected by, for example, aggregation of particles bearing the binding partners. Binding can be detected by methods well known in the an (e.g., radioactive or fluorescent labeling of one component of the potential binding pair; plasmon-resonance detection of binding; turbidity changes in aggregation assays). Compounds which, under physiological conditions (e.g., within the testis or epididymis, or within the vagina, uterus or fallopian tubes), exhibit significant binding (e.g., $K_d \leq 10$ µM) to a CatSper2 protein, are potential modulators of CatSper2 activity.

Methods of Modulating Fertility.

The CatSper2 gene and proton are ideal targets for potential contraceptive drugs. Since the CatSper2 protein is expressed in the flagella of sperm, a specific blocker of CatSper2 can inhibit sperm motility, and thus can be effective as a contraceptive when used by either sex. The restricted localization of CatSper2 to sperm and spermatogenic cells means that a specific blocker should not affect other tissues and thus side effects should be low or nonexistent. Finally, because the channel represents a novel structure, it can be an excellent target for new channel agonists or antagonists.

Thus, in another aspect, the present invention provides methods of decreasing fertility by decreasing the expression or activity of a CatSper2 gene or protein. Such decreases in expression or activity can be achieved by means of a small molecule that represses expression of a CatSper2 gene, by means of an antisense molecule that inhibits the translation of a CatSper2 mRNA, by means of a small molecule that interferes with CatSper2 translation or post-translational processing, by means of a small molecule that interferes with CatSper2 localization, by means of a molecule that blocks CatSper2 activity as an ion channel, or by any other molecule that decreases the expression of a CatSper2 gene or hastens CatSper2 protein degradation. Antibodies, including antibody fragments such as Fab, $F(ab')_2$ or Fv fragments, and single-chain Fv (scFv) fragments that specifically bind to CatSper2 protein or polypeptides, also can be used to inhibit CatSper2 activity by binding to extracellular domains of the protein and thereby block its activity.

Because most repressors or antagonists of CatSper2 expression or activity will be reversible or will affect only mature sperm, the effects of such compounds on fertility will be reversible because the molecules will be cleared from the body over time and new sperm are constantly being produced. Thus, repressors or antagonists of CatSper2 expression or activity can be used as human contraceptives because they can cause reversible infertility. Such contraceptives can be taken orally or parenterally (e.g., injection, transdermal patch, or bioerodable implant) by females if they achieve sufficient concentrations in the vagina, uterus or fallopian tubes to effectively inhibit CatSper2 activity and thereby decrease sperm motility or the ability of sperm to penetrate the ZP. Similarly, such contraceptives can be taken orally or parenterally by males if they achieve sufficient concentration in the testes or seminal fluids to effectively inhibit CatSper2 expression or activity, and thereby decrease sperm motility or the ability of sperm to penetrate the ZP. Alternatively, such compounds can be formulated into lubricants, moisturizers, foams or jellies for use with prophylactics, cervical caps, or contraceptive vaginal sponges, foams or jellies.

In another series of embodiments, repressors or antagonists of CatSper2 genes and proteins can be used as contraceptives to treat non-human mammals. These embodiments are similar to those described above. Such contraceptives can be used with respect to domesticated animals which are maintained as pets, with respect to commercially valuable domesticated animals (e.g., cows, sheep, horses), or with respect to animal nuisances (e.g., mice, rats, raccoons, gophers). In some embodiments, the contraceptives are orally available and can be mixed into food sources for the animals. In other embodiments, the contraceptives can be administered parenterally (e.g., injection, transdermal patch, or bioerodable implant).

To the extent that the mammalian CatSper2 genes and proteins and the fish, amphibian and insect homologs of the CatSper2 genes and proteins share substantial sequence identity, repressors or antagonists of mammalian CatSper2 genes and proteins can also be used in the control of fish, amphibian and insect nuisances (e.g., mosquitoes). In addition, the non-mammalian homologs of the CatSper2 genes and proteins can be used to identify additional repressors and antagonists which are more specific or effective for such homologs.

Methods of CatSper2 Genotyping and Diagnosing CatSper2-Related Disorders.

In another aspect, the present invention provides methods for genotyping subjects with respect to the CatSper2 gene, and diagnosing CatSper2-related disorders such as infertility. Thus, for example, the CatSper2 nucleic acids (or a portion thereof) of a subject can be tested to ascertain whether that subject's CatSper2 genotype includes any mutations in the sequences relative to wild-type. Of particular significance would be mutations which introduce termination or frame-shift mutations that prevent the production of functional CatSper2 proteins. However, point mutations that cause decreased CatSper2 activity can also be identified. Similarly, the antibodies of the present invention can be used to test the sperm of a subject to determine the presence or level of CatSper2 proteins. Of particular note would be an absence or significant decrease in the level of CatSper2 protein. Point mutations, however, can also cause infertility and can be detected by antibodies which are specific for epitopes including or affected by the mutant sequences. Determination of a subject's CatSper2 genotype can be used for generic or reproductive counseling, or for diagnosing infertility that results from a CatSper2 defect.

To determine a subject's CatSper2 genotype, or for diagnosing a CatSper2-related disorder, the nucleic acids of the invention can be used as primers in polymerase chain reaction (PCR) (e.g., anchor PCR or RACE PCR), or ligase chain reaction (LCR) amplifications of the subject's DNA/mRNA. See, e.g., U.S. Pat. No. 4,683,195 and U.S. Pat. No. 4,683,202; Landegran et al. (1988), *Science* 241:1077-1080; Nakazawa et al. (1994), *Proc. Natl. Acad. Sci. USA* 91:360-364; and Abravaya et al. (1995), *Nucleic Acids Res.* 23:675-642. Other useful methods for amplifying a subjects DNA/mRNA using the nucleic acids of the invention include self-sustained sequence replication (e.g., Guatelli et al. (1990), *Proc. Natl. Acad. Sci. USA* 87:1874-1878), transcriptional amplification (e.g., Kwoh et al. (1989), *Proc. Natl. Acad. Sci. USA* 86-1173-1177), and Q-Beta Replicase-based systems (e.g., Lizardi et al. (1988), *Bio/Technology* 6:1197. The presence, absence or size of the resulting amplification products (e.g., Saiki et al. (1986), *Nature* 324:163; Saiki et al. (1989), *Proc. Natl. Acad. Sci. USA* 86:6230; Gibbs et al. (1989), *Nucleic Acids Res.* 17:2437-2448; Prossner (1993), *Tibtech* 11:238; Gasparini et al.

(1992), *Mol. Cell Probes* 6:1, Barany 1991) *Proc. Natl. Acad. Sci. USA* 88:189), direct sequencing of the amplification products (e.g., Maxim and Gilbert (1977), *Proc. Natl. Acad. Sci. USA* 74:560; Sanger (1977), *Proc. Natl. Acad. Sci. USA* 74:5463), and other standard analytic techniques can be employed to determine CatSper2 genotypes. The amplified products can also be used in many of the techniques described below.

The nucleic acids of the invention also can be used as probes in hybridization and/or conformation-based assays to identify complementary or imperfectly complementary sequences in a subject.

For example, in some embodiments, mutations can be identified by selectively hybridizing sample nucleic acids to immobilized control nucleic acids. The controls can be adsorbed to filters or columns, or can be arranged in high density ordered arrays containing hundreds or thousands of oligonucleotides probes (see, e.g., Cronin et al. (1996), *Human Mutation* 7:244-255; Kozal et al. (1996), *Nature Medicine* 2:753-759).

In other embodiments, enzymatic or chemical cleavage can be employed to cleave or restrict duplexes of sample and control sequences at mismatched bases (e.g., Myers et al. (1985), *Science* 230:1242). For example, RNA/DNA duplexes can be treated with RNAse; DNA/DNA hybrids can be treated with S1 nuclease to digest duplexes at mismatched bases; G/A mismatches are cleaved at the A by the *E. coli* mutY enzyme; and G/T mismatches are cleaved at the T by the human thymidine DNA glycosylase (see, e.g., Hsu et al. (1994), *Carcinogenesis* 15:1657-1662). Chemical cleavage of mismatches can be employed using, for example, hydroxylamine, osmium terroxide and/or piperidine. See generally, e.g., Cotton et al. (1988), *Proc. Natl. Acad. Sci. USA* 85:4397; Saleeba et al. (1992), *Methods Enzymol.* 217:286-295; and U.S. Pat. No. 5,459,039.

In other embodiments, mutations can create or destroy specific sequences which serve as cleavage points for restriction enzymes or ribozymes. Thus, restriction fragment length polymorphism (RFLP) analysis can be employed in which (amplified) sample DNA is digested with at least one restriction endonuclease, and the resulting fragment lengths are analyzed and compared to controls to determine the presence or absence of mutations which affect the pattern of restriction fragment lengths. Similarly, sequence-specific ribozymes can be used to identify mutations that create or destroy ribozyme cleavage sites. See, e.g., U.S. Pat. No. 5,498,531.

In other embodiments, mutations can be detected by their effects on the electrophoretic mobility of a sequence, either as a single-stranded nucleic acid or as a duplex. For example, single-strand conformation polymorphism (SSCP) analysis (Orita et al. (1989), *Proc. Natl. Acad. Sci. USA* 86:2766; Cotton (1993), *Mutat. Res.* 285:125-144; Hayashi (1992), *Genet. Anal. Tech. Appl.* 9:73-79; and Keen et al. (1991), *Trends Genet.* 7:5), denaturing gradient gel electrophoresis (DGGE) (Myers et al. (1985), *Nature* 313:495), and temperature gradient gel electrophoresis (Rosenbaum and Reissner (1987), *Biophys. Chem.* 265:12753) can be employed.

These and other methods of detecting mutations in the CatSper2 genes and proteins will be apparent to one of ordinary skill in the art based upon the nucleic acid and protein sequences disclosed herein.

In Vitro Fertilization

In another aspect, the present invention provides a method of in vitro fertilization of ova by sperm characterized by decreased CatSper2 expression or activity. Because of the role of CatSper2 in the flagellum, CatSper2-deficient sperm will be compromised in their motility and, therefore, their ability to fertilize ova. In particular, proper flagellar function is necessary for sperm to penetrate the Zona Pellucida (ZP) for fertilization (Ren et al. (2001), supra). Thus, the present invention provides a method of in vitro fertilization for CatSper2-deficient males in which the sperms of such males are treated to overcome the CatSper2 deficiency or are contacted with ova from which the ZP have been removed. Because other genetic deficiencies can result in sperm which are incapable of penetrating the ZP, this method can be extended to other males having genetic deficiencies which affect sperm motility or ZP-penetration, or for which in vitro fertilization previously has been unsuccessful using ova with intact ZPs.

Methods of Treating CatSper2-Mediated Infertility.

In another aspect, the present invention provides methods of treating infertility in CatSper2-deficient males, in which an enhancer of CatSper2 expression or an agonist of CatSper2 activity is administered to the subject. In other embodiments, gene or protein therapy can be employed to provide the Catsper2 gene or protein to sperm (or sperm progenitors) which are deficient in the CatSper2 gene or protein. For gene therapy, a genetic construct encoding a CatSper2 protein can be employed to cause expression of a CatSper2 protein in sperm or sperm progenitors which are deficient in the CatSper2 gene or protein.

In another aspect, infertility of a mating pair (e.g., a human couple) can result from antibodies generated by the female against antigens present on the sperm of the male. In some cases, the antibodies can be directed against an epitope of a CatSper2 protein. Thus, the present invention also provides methods of diagnosing an anti-CatSper2 antibody-mediated infertility caused by anti-CatSper2 antibodies present in a female urogenital tract. The methods include obtaining a sample of antibodies present in the female and contacting the antibodies with CatSper2 proteins or fragments of CatSper2 proteins. In some embodiments, the CatSper2 fragments are epitopes of the CatSper2 proteins having high predicted antigenicity (e.g., approximately residues 266-275, 386-400, 447-458, and 482-494 of SEQ ID NO: 2; approximately residues 66-99, 256-275, and 394-414 of SEQ ID NO: 4; approximately residues 64-89, 262-275 and 562-588 of SEQ ID NO: 6, and allelic and mammalian homologs thereof). In these methods, either the female's antibodies or the CatSper2 proteins/fragments optionally can be immobilized and either the female's antibodies or the CatSper2 proteins/fragments optionally can be detectably labeled to facilitate detection of binding between the antibodies and the CatSper2 proteins/fragments.

In these cases, administering an excess of the CatSper2 protein, or at least a fragment of the CatSper2 protein including the relevant epitope, can saturate the binding sites of the anti-CatSper2 antibodies present in the female's urogenital tract and thereby inhibit or reduce the antibody-mediated infertility. Alternatively, an anti-idiotypic antibody (i.e., an antibody which specifically binds to the variable regions of another antibody with a defined specificity) can be employed. That is, an antibody which binds specifically to anti-CatSper2 antibodies can be employed to inhibit the anti-CatSper2 antibodies present in the female's urogenital tract and thereby inhibit or reduce the antibody-mediated infertility. One of ordinary skill in the art can easily identify the relevant CatSper2 epitopes recognized by such female antibodies (e.g., using the methods described above) and produce substantially pure preparations of the relevant epitope or anti-idiotypic antibodies by standard means.

Thus, the invention also provides methods for treating air anti-CatSper2 antibody-mediated infertility caused by anti-CatSper2 antibodies present in a female urogenital tract. The methods include administering into the urogenital tract of the female an amount of the relevant CatSper2 epitope (or whole CatSper2 protein) or an amount an anti-idiotypic antibody effective to inhibit the anti-CatSper2 antibodies and thereby inhibit or reduce the antibody-mediated infertility.

Business Methods Relating to CatSper2.

In another aspect, the present invention provides a method of conducting a drug discovery business comprising: identifying, by the assays of the invention, one or more agents which antagonize CatSper2 activity; determining if an agent identified in such an assay, or an analog of such an agent, inhibits at least one of sperm motility or egg penetrance; conducting therapeutic profiling of an agent identified as an antagonist for efficacy and toxicity in one or more animal models; and formulating a pharmaceutical preparation including one or more antagonist agents identified as having an acceptable therapeutic profile.

In one embodiment, the drug discovery business further includes the step of establishing a system for distributing the pharmaceutical preparation for sale, and can optionally include establishing a sales group for marketing the pharmaceutical preparation.

In another aspect, the present invention provides a method of conducting a drag discovery business comprising: identifying, by the subject assay, one or more agents which agonize CatSper2 activity; determining if an agent identified in such an assay, or an analog of such an agent, increases at least one of sperm motility or egg penetrance; conducting therapeutic profiling of an agent identified as an agonist for efficacy and toxicity in one or more animal models; and formulating a pharmaceutical preparation including one or more agents identified as having an acceptable therapeutic profile.

In certain embodiments, the drug discovery business further includes the step of establishing a system for distributing the pharmaceutical preparation for sale, and can optionally include establishing a sales group for marketing the pharmaceutical preparation.

In certain embodiments, the assay to identify agents which agonize CatSper2 activity is conducted using wild type CatSper2. In another embodiment, the assay to identify agents which agonize CatSper2 activity is conducted using a mutant CatSper2. By a "mutant CatSper2" is meant a CatSper2 polypeptide containing one or more amino acid insertions, deletions, or substitutions, wherein said insertions, deletions, or substitutions change the amino acid sequence and activity of the mutant CatSper2 in comparison to wild type CatSper2. Such a change in activity can include, but is not limited to, a change in motility, egg penetrance, or cation transport. A change in activity could also include a change in the proper localization or expression of the CatSper2 protein or mRNA.

In still another aspect, the invention provides a method of conducting a reproductive medicine business comprising: examining a sperm sample from a male patient, wherein said patient is experiencing a fertility problem; determining if said sperm are characterized by at least one of a decrease in motility or a decrease in egg penetrance: performing in vitro analysis to determine the efficacy of a CatSper2 agonist in increasing at least one of sperm motility or egg penetrance; establishing a treatment regimen comprising administering an amount of a CatSper2 agonist effective to increase at least one of sperm motility or egg penetrance by sperm from the male.

In certain embodiments, the method further includes a step wherein the male patient is monitored by a physician to evaluate improvement in fertility. Such evaluation can include examination of sperm at regular intervals following the initiation of treatment to measure improvements in one or more of sperm motility or egg penetrance. The frequency of follow-up evaluation by the treating physician will be determined by the physician or a trained health care provider. Factors to consider are the patient's schedule and comfort level, as well as the urgency with which a male patient is attempting to father an offspring. Representative follow-up appointments can be conducted weekly, semi-weekly, or monthly. In another embodiment, the method further includes the step of billing the patient or the patient's insurance provider. In cases where the patient's health insurance is paying for all or a portion of the fertility treatments, the policies of the health insurance provider will likely influence the frequency of follow-up appointments.

In yet another aspect, the present invention provides a method of conducting a contraceptive medicine business comprising: providing a pharmaceutical preparation discovered through the methods of a drug discovery business, wherein said preparation inhibits the activity of CatSper2 providing instructions to physicians and health care providers for the administration of an amount of said pharmaceutical preparation effective to inhibit the activity of CatSper2, wherein said effective amount is sufficient to prevent pregnancy.

In one embodiment, the method farther includes the step of establishing a system for distributing the pharmaceutical preparation for sale, and can optionally include establishing a sales group for marketing the pharmaceutical preparation.

CatSper2 encodes a cation channel. Numerous types of cation channels play critical roles in cellular processes Including regulation of cardiac function (e.g., calcium channels). Thus, a great limitation of methods which employ administration of agents which either increase or decrease the activity of cation channels is that such methods are likely to have substantial side-effects. These side-effects can include significant cardiac complications. However, the results provided herein demonstrate that CatSper2 is specifically expressed in sperm. Accordingly, agents which selectively increase or decrease the activity of CatSper2 can be administered to patients without the side effects associated with either general canon channel antagonists and agonists, or antagonists and agonists of canon channels which are more widely expressed in the body.

Through a drug discovery business, one or more agents which can antagonize the activity of CatSper2 can be identified. By antagonize the activity is meant to decrease, in whole or in part, the activity of CatSper2. Such a decrease in activity can be measured by examining at least one of sperm motility, egg penetrance, or cation transport. The terms decrease and antagonize will be used interchangeably throughout.

In certain embodiments, the initially identified CatSper2 agonist or antagonist can be subjected to further lead optimization, e.g., to further refine the structure of a lead compound so that potency and activity are maintained but balanced with important pharmacological characteristics including: solubility, permeability, bioavailability, toxicity, mutagenicity, and pharmacokinetics (e.g., absorption, distribution, metabolism, elimination). Structural modifications are made to a lead compound to address issues with these pharmacological parameters. These modifications however, most take into account possible effects on the molecule's potency and activity. For example, if the solubility of a lead compound is poor, changes can be made to the molecule in as effort to improve solubility; these modifications, however, can negatively affect the molecule's potency and activity. Structure-activity relationship (SAR) data are then used to determine the effect of the change upon potency and activity. Using an iterative process of structural modifications and SAR data, a balance is created between these pharmacological parameters and the potency and activity of the compound.

Candidate antagonists, or combinations thereof, must then be tested for efficacy and toxicity in animal models. Such therapeutic profiling is commonly employed in the pharmaceutical arts. Before testing an experimental drag in humans, extensive therapeutic profiling (e.g., preclinical testing) must be completed to establish initial parameters for safety and efficacy. Preclinical testing establishes a mechanism of action for the drug, its bioavailability, absorption, distribution, metabolism, and elimination through studies performed in vitro (that is, in test tubes, beakers, petri dishes, etc.) and in animals. Animal studies are used to assess whether the drug will provide the desired results. Varying doses of the experimental drug are administered to test the drug's efficacy, identify harmful side-effects that may occur, and evaluate toxicity.

Briefly, one of skill in the art will recognize that the identification of a candidate agent which antagonizes CatSper2 activity in a drug-based screen is a first step in developing a pharmaceutical preparation useful as a contraceptive agent. Administration of an amount of said pharmaceutical preparation effective to successfully prevent pregnancy (e.g., to act as a useful contraceptive agent) must be both safe and effective. Early stage drag trials, routinely used in the art, help to address concerns of the safety and efficacy of a potential pharmaceutical. In the specific case of a CatSper2 antagonist, efficacy of the pharmaceutical preparation could be readily evaluated in a mouse or rat model. Briefly, male mice could be administered varying doses of the pharmaceutical preparations over various time schedules. Control male mice can be administered a placebo (e.g., carrier or excipient alone). The male mice are then allowed to mate freely by placing the males into cages with female mice, and measuring the rate of conception over time. Given the efficacy of currently available forms of birth control, an effective contraceptive should be at least 80%, 85%, 90%, 95%, 99%, or greater than 99% effective in preventing pregnancy.

In one embodiment, the step of therapeutic profiling includes toxicity testing of compounds in cell cultures and in animals, analysis of pharmacokinetics and metabolism of the candidate drug; and determination of efficacy in animal models of diseases. In certain instances, the method can include analyzing SARs and optimizing lead structures based on efficacy, safety and pharmacokinetic profiles. The goal of such steps is the selection of drug candidates for pre-clinical studies to lead to filing of Investigational New Drug ("IND") applications with the U.S. FDA and/or similar applications with similar regulatory authorities prior to human clinical trials.

Between lead optimization and therapeutic profiling, one goat of the subject method is to develop a CatSper2 agonist or antagonist which has minimal side-effects. In the case of antagonists, the lead compounds will have clinically acceptable effects on vasodilatation (i.e., dizziness, hypotension, headache, flushing, edema, etc.), myocardial ischemia, hypotension, bradycardia, transient asystole, exacerbation of heart failure, ventricular dysfunction, SA node or AV conduction disturbances, or plasma digoxin levels.

By "toxicity profiling" is meant the evaluation of potentially harmful side-effects which may occur when an effective amount of a pharmaceutical preparation is administered. A side-effect may or may not be harmful, and the determination of whether a side effect associated with a pharmaceutical preparation is an acceptable side effect is made during the regulatory approval process. Acceptable side effects vary due to factors including: (a) the seventy of the condition being treated, and (b) the availability of other treatments and the side-effects currently associated with these other treatments. For example, the term cancer encompasses a complex family of disease states related to misregulated cell growth, proliferation, and differentiation. Many forms of cancer are particularly devastating diseases which cause severe pain, loss of function of the effected tissue, and death. Chemotherapeutic drugs are an important part of the standard therapy for many forms of cancer. Although chemotherapeutics themselves can have serious side-effects including hair-loss, severe nausea, weight-loss, and sterility, such side-effects are considered acceptable given the severity of the disease they aim to treat.

In contrast, however, most currently available forms of birth control do not have significant side-effects. Thus, a pharmaceutical preparation of a CatSper2 antagonist should have minimal toxicity and side-effects. Toxicity tests can be conducted in tandem with efficacy tests, and male mice administered effective doses of the pharmaceutical preparation can be monitored for adverse reactions to the preparation. Potential adverse reactions associated with a contraceptive agent may include loss of sex drive, and behavioral changes. Blood, urine, and fecal samples taken from treated mice can also be monitored to detect any potential adverse changes in immune, kidney, or liver function. Additionally, given that CatSper2 is a cation channel, mice receiving said pharmaceutical preparation should also be monitored for any changes in cardiac function indicative of cross reactivity of the CatSper2 antagonist with other canon channels.

Agents which antagonize CatSper2 activity, and which are proven safe and effective in animal studies, can be formulated into a pharmaceutical preparation. Such pharmaceutical preparations can then be marketed, distributed, and sold as contraceptive agents.

Given the link between loss of CatSper2 activity and fertility, there is substantial utility in agents which increase the activity of CatSper2 to treat male fertility problems. Many instances of infertility involve problems linked to the male. Such male infertility issues include low sperm count, poor sperm motility, and abnormal sperm morphology. Currently there are few effective treatments for male-associated infertility.

The first step in developing potentially successful treatments for male infertility is the identification of CatSper2 agonists. A CatSper2 agonist is one or more agents which increase the activity of CatSper2. As outlined in detail above for CatSper2 antagonists, agonists of the CatSper2 protein are expected to have fewer potential side-effects than other cation channel agonists.

Methods for identifying agents which act as CatSper2 agonists are performed largely as detailed for CatSper2 antagonists. However, a useful CatSper2 agonist will increase one or more of sperm motility or egg penetrance. Additionally, when identifying a CatSper2 agonist, such an agent can agonize the activity of a wild type CatSper2. In addition, or alternatively, such an agent can agonize the activity of a mutant CatSper2. One or more agonists identified by these methods can then be tested for safety and efficacy, as outline in detail above. Agents which are shown to be safe and effective in animal studies are formulated into a pharmaceutical preparation.

CatSper2 agonists are not likely to be effective for treating all male fertility problems. However, it is expected that some undetermined percentage of male fertility problems will be amenable to treatment using agonists of CatSper2 function. For example, a certain percentage of male infertility which results in poor sperm motility is likely due to mutations in CatSper2. Given that CatSper2 is expressed specifically in sperm, males possessing such a mutation would be expected to have little or no additional medical problems, and this explains in part why infertility is often found in otherwise healthy men. Additionally, a CatSper2 agonist can improve sperm motility overall, and thus help compensate for poor sperm motility due to other unrelated causes.

Conducting a Reproductive Medicine Business.

A pharmaceutical preparation including one or more agents which agonize the activity of a wild type or mutant CatSper2 can be useful in establishing a reproductive medicine business which provides treatment for candidate male patients experiencing fertility difficulties. Sperm samples provided by male patients are examined to determine if infertility in the male patients is amenable to treatment with the pharmaceutical preparation. Patients whose sperm is characterized by a decrease in at least one of motility or egg penetrance can be eligible for treatment. Prior to treatment, sperm samples provided by the male patients are tested in vitro with the pharmaceutical preparation to further assess whether the male is eligible for treatment. This additional step of in vitro testing helps to alleviate unnecessary treatment in males whose infertility is unlikely to be improved with the CatSper2 agonist.

Male patients whose sperm shows increased motility or egg penetrance in vitro are eligible for fertility treatment including the pharmaceutical preparation including one or more CatSper2 agonist. The exact treatment regimen will vary from patient to patient, and can be readily determined by an experienced medical professional. However, the treatment regimen will include administration of an amount of said pharmaceutical preparation effective to increase at least one of sperm motility or egg penetrance in said treated male. In certain embodiments, the increase in sperm motility or egg penetrance will result in an increase in fertility.

Pharmaceutical Preparations.

In another aspect, the invention provides pharmaceutically acceptable preparations comprising a therapeutically effective amount of one or more of the identified agents (i.e., antagonists or agonists) described above, formulated together with one or more pharmaceutically acceptable carriers (additives) and/or diluents. As described in detail below, the pharmaceutical compositions of the present invention can be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds can be simply dissolved or suspended in sterile water.

The phrase "therapeutically effective amount" as used herein means that amount of an agent or composition which is effective for producing some desired therapeutic effect, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject antagonists from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes: (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water, (17) isotonic saline; (18) Ringer's solution; (19) ethyl alcohol; (20) phosphate buffer solutions; and (21) other non-toxic compatible substances employed in pharmaceutical formulations. In certain embodiments, the pharmaceutical preparation is non-pyrogenic, i.e., does not elevate the body temperature of a patient.

The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, for example, Berge et al. (1977), *J. Pharm. Sci*, 66:1-19.)

The pharmaceutically acceptable salts of the subject agents include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the agents of the present invention can contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the agents, or by separately reacting the purified agent in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al. (1977), supra)

Wetting agents, emulsifiers and lubricants, such as sodium, lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations can conveniently be presented in unit dosage form and can be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, this amount, will range from about 1% to about 99% of active ingredient, from about 5% to about 70%, or from about 10% to about 30%.

Methods of preparing these formulations or compositions include the step of bringing into association one or more agents of the present invention with the carrier and, optionally, one or more accessory ingredients. In general, the formulations are prepared by uniformly and intimately bringing into association one or more agents of the present invention with liquid carriers, or finely divided solid carriers, or both, and then, if necessary, shaping the product.

Formulations of the invention suitable for oral administration can be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. An agent of the present invention can also be administered as a bolus, electuary or paste.

In solid dosage forms of the invention for oral administration (capsules, tablets, pills, dragees, powders, granules and the like), the active, ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions can also comprise buttering agents. Solid compositions of a similar type can also be employed as fillers in soft and hard-filled gelatin capsules using such excipients as lactose or milk sugars, as well as high molecular weight polyethylene glycols and the like.

A tablet can be made by compression or molding, optionally with one or more accessory ingredients. Compressed tablets can be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets can be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They can also be formulated so as to provide slow or controlled release of the active ingredient therein using, for example, hydroxypropylmethyl cellulose in varying proportions to provide the desired release profile, other polymer matrices, liposomes and/or microspheres. They can be sterilized by, for example, filtration through a bacteria-retaining filter, or by incorporating sterilizing agents in the form of sterile solid compositions which can be dissolved in sterile water, or some other sterile injectable medium immediately before use. These compositions can also optionally contain opacifying agents and can be of such a composition that they release the active ingredients) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms can contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration can be presented as a suppository, which can be prepared by mixing one or more agents of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include peccaries, tampons, creams, gels, pastes, foams or spray formulations containing such carriers as are known in the art to be appropriate.

Dosage forms for the topical or transdermal administration of one or more agents of this invention include powders, sprays, ointments, pastes, creams, lotions, gels, solutions, patches and inhalants. The active agents can be mixed under sterile conditions with a pharmaceutically acceptable carrier, and with any preservatives, buffers, or propellants which may be required.

The ointments, pastes, creams and gels can contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of an agent of the present invention to the body. Such dosage forms can be made by dissolving or dispersing the subject compound in the proper medium. Absorption enhancers can also be used to increase the flux of the subject agent across the skin. The rate of such flux can be controlled by either providing a rate controlling membrane or dispersing the compound in a polymer matrix or gel.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which can be reconstituted into sterile injectable solutions or dispersions just prior to use, which can contain antioxidants, buffers, bacteriostats, solutes which render the formulation isotonic with the blood of the intended recipient or suspending or thickening agents.

Examples of suitable aqueous and nonaqueous carriers which can be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

When the compounds of the present invention are administered as pharmaceuticals, to humans and animals, they can be given per se or as a pharmaceutical composition containing, for example, 0.1 to 99.5%, or 0.5 to 90%, of active ingredient in combination with a pharmaceutically acceptable carrier.

The following examples illustrate some specific modes of practicing the present invention, but are not intended to limit the scope of the claimed invention. Alternative materials and methods can be utilized to obtain similar results.

EXAMPLE 1

Preparation of cDNA Library

An enriched spermatid cell fraction from mouse 129Sv/Ev adult testes was prepared using the unit gravity sedimentation method of Bellve (1993), *Methods Enzymol.* 225:84-113. Poly $A^+$ RNA from the preparation was reverse transcribed with random primers to synthesize double-stranded cDNA according to the suppliers protocol (Life Technologies/Invitrogen Corp., Carlsbad, Calif.). This cDNA (2 µg) was then subjected to suppression subtraction hybridization (PCR Select™, Clontech, Palo Alto, Calif.) using driver cDNA (2 µg) prepared from a mixture of equal amounts of poly $A^+$ RNA from nine different enriched tissues including brain, heart, intestine, kidney, liver, lung, skeletal muscle, spleen, and stomach. The resulting cDNA sample was subcloned into the signal peptide trapping vector NotI site following digestion with EagI, and was transformed into XL-10 Gold competent bacteria (Stratagene, La Jolla, Calif.) for amplification.

EXAMPLE 2

Signal Peptide Trapping

A. Vector Preparation.

The *Saccharomyces cerevisiae* invertase gene (Genbank Accession No. NC_001141.1, nucleotides 36484-37357 and 37448-39483 including the promoter, coding sequence without the signal peptide, and termination signals) was subcloned as an EcoRI/SalI fragment from pRB576 into the pBluescript™ plasmid (Stratagene, La Jolla, Calif.). The invertase coding sequence was modified by site-directed mutagenesis (Quikchange, Stratagene, La Jolla, Calif.) to replace the initiation methionine codon of the cytoplasmic enzyme form with an alanine, and an artificial linker containing NotI and SalI cloning sites, was ligated into the HindIII-SmaI site at the start of the invertase coding sequence. This modified invertase gene was subcloned into the yeast shuttle, vector pYEUra3 (Genbank Accession No. (J02457) using the EcoRI and XhoI restriction sites to produce pSPT IB.

B. Yeast Transformation and Selection.

Signal peptide trapping was performed essentially as described by Klein et al. (1996), *Proc. Natl. Acad. Sci. USA* 93:7108-13. Briefly, the yeast strain YT455 (suc2Δ9, ade2-101, ura3-52) was transformed with the enriched spermatid cDNA library using lithium acetate. The resulting transformants were selected on minimal medium/-Ura dropout plates for three clays at 30° C. and then replica plated onto YPS plates (2% sucrose as the sole carbon source) to select for cDNA that encoded functional signal peptides. Those yeast colonies that grew on sucrose over days were analyzed for cDNA inserts.

C. Sequence Analysis.

Plasmids were released from yeast minicultures by lysis with SDS and glass beads (Strathern and Higgins (1991), *Methods Enzymol.* 194:319-29). The cDNA inserts were amplified by PCR using vector-specific primers flanking the cloning site. The resulting PCR products were subjected to automated sequencing followed by BLAST analysts against the GenBank database (Altschul et al. (1997), *Nucleic Acid Res.* 25:3389-3402).

D. Identification of CatSper2 Clone.

An enriched spermatid cDNA library was screened using a yeast-based signal peptide selection method (Klein et al. (1995), supra; Jacobs et al. (1997), *Gene* 198:289-96.). $1.2 \times 10^6$ colonies containing mouse spermatid cDNAs were screened. Approximately 350 revertant yeast colonies were obtained after selection on sucrose. Of these selected cDNA clones, several known membrane/secreted proteins specifically expressed by sperm were identified (e.g., sp56, ferrilin β, ADAM 26, TPX-1) demonstrating the validity of the technique. A novel cDNA sequence encoding a protein with a deduced topology similar to the voltage-gated potassium channels but containing a pore with calcium selectivity was identified and subsequently designated CatSper2.

EXAMPLE 3

Identification of Complete CatSper2 cDNA Sequences

The complete coding sequence of the clone was determined using cDNA fragment-specific antisense and sense primers for 5' and 3' RACE amplifications, respectively (Marathon Ready Mouse™ Testis cDNA, Clontech, Palo Alto, Calif.). An intact full-length clone was produced using PCR with a specific 5' and 3' UTR primer pair. The resulting PCR product was subcloned into pCR 2.1 (Stratagene, La Jolla, Calif.) and sequenced to verify the absence of mutations.

A full-length cDNA containing 1986 bp was isolated using RACE. The predicted ORF encodes a 588 amino acid protein with six transmembrane segments (FIG. 1(A)). The fourth transmembrane segment contains basic amino acid residues (K/R) spaced at every fourth position, characteristic of voltage-gated ion channels. A BLAST comparison of this sequence with the Genbank database revealed similarity to the voltage-gated calcium channel family (Calif.). The $Na_v$, $K_v$, cyclic nucleotide-gated (CNG), transient receptor potential (TRP), and polycystin channels appeared more distantly related. Among the known proteins, CatSper2 is most similar to CatSper1, another sperm cell-specific putative cation channel recently found important for motility and normal fertilization (FIG. 1(B); Ren et al. (2001), supra). These two proteins are 21% identical and 40% similar within the transmembrane region. The selectivity of ion channels is determined by the pore-forming residues located between the fifth (S5) and sixth (S6) transmembrane, segments. As shown in FIG. 1(B), several amino acid residues in the pore (P) region are conserved between CatSper2, CatSper1, and the $Ca_v$ channels including a critical aspartic or glutamic acid residue that defines calcium selectivity (Varadi et al. (1999), *Crit. Rev. Biochem. Mol. Biol.* 34:181-214). The cytoplasmic portion of CatSper2 following the transmembrane region contains additional potential functional motifs. The repetitive sequence region contains multiple candidate tyrosine phosphorylation sites suggesting that CatSper2 may represent one of the proteins phosphorylated during capacitation in the mouse (Visconti et al. (1995), *Development* 121:1129-37). The C-terminal cytoplasmic region also contains an unconventional leucine zipper motif from residues 547-568 (Marx et al. (2001), *J. Cell Biol.* 153:699-708). This region may mediate protein-protein interactions that form the actual channel pore complex, or that modulate CatSper2 channel activity in sperm cells.

Using the mouse CatSper2 sequence, three similar cDNA sequences encoding proteins with the same predicted topology as CatSper2 were cloned from human testis. The proteins encoded by the human clones are 63-67% identical overall with mouse CatSper2. Two of the human clones encode predicted ORFs of 528 (SEQ ID NO: 2) and 530 amino acids and differ from each other only by the presence of two tandem serine residues 54 amino acid residues after the transmembrane region (i.e., two serine residues are inserted between residues 392 and 393 of SEQ ID NO: 2). The third human clone encodes a predicted ORF of 414 amino acids (SEQ ID NO: 4), identical to the other human clones until amino acid residue 393, where a 211 nucleotide gap in the cDNA sequence causes a frameshaft and early termination. The transmembrane region of all three human proteins is 77% identical to mouse CatSper2, including an identical P region. The cytoplasmic region before the transmembrane segments and the carboxy terminal 63 amino acids of CatSper2 are also conserved in the two longer human homologs, 73% and 90% identical, respectively.

EXAMPLE 4

Northern Blot Analysis

Total RNA (15 µg) from several mouse tissues and poly $A^+$ RNA (2 µg) from mouse, rat, and human testes were separated on 1% agarose MOPS/formaldehyde gels (Sambrook et al (1989), supra). Following transfer to positively charged nylon membranes, the blots were hybridized overnight at 42° C. with either a random-primed $^{32}P$ probe corresponding to nucleotides 113-531 of the cDNA sequence (mouse tissue blot) or nucleotides 919-1299 (cross-species blot: mouse, tat, and human) at $10^6$ cpm/ml in ULTRAhyb™ (Ambion, Inc., Austin, Tex.). The blot was washed with 0.1×SSC/0.2% SDS/0.1% $NaPP_1$ (1×15 min at room temperature, 3×15 rain at 65° C.) and exposed to film.

Northern blot analysts with a CatSper2 cDNA probe detected a single 2.1 kb transcript in mouse testis. No signal was detected in other tissues examined (brain, heart, intestine, kidney, liver, ovary, skeletal muscle, spleen, stomach), even with a sensitive RT-PCR assay. This result, along with the presence of in-frame stop codons upstream of the putative initiation methionine, indicates that the transcript is full-length. CatSper2 mRNA also was identified as a 2.0-2.1 kb transcript in both rat and human testis samples.

By in situ hybridization of testicular tissue, it was shown that meiotic and post-meiotic cells contained the CatSper2 transcript. Paraformaldehyde-fixed, paraffin-embedded mouse testis sections were probed with $^{35}$S labeled CatSper2 sense or antisense probes (nucleotides 113-531) and examined by bright field and dark field microscopy. The antisense probe hybridized to the seminiferous tubules over both spermatocytes and spermatids. There were no positive signals in other cells, and the sense probe also failed to hybridize to any testicular cell type.

EXAMPLE 5

In Situ Hybridization

The region corresponding to nucleotides 113-531 was amplified by PCR and subcloned into pCR 4.0-TOPO (Invitrogen Corporation, San Diego, Calif.). Radiolabeled ($^{35}$S) cRNA sense and antisense probes were transcribed from the linearized plasmid (MAXIscript™, Ambion, Inc., Austin, Tex.). In situ hybridization of adult mouse testis sections was performed according to Shelton et al. (2000), *J. Lipid Res.* 41:532-7.

EXAMPLE 6

Production of Peptide Antibody

Antibodies were made to synthetic peptides corresponding to amino acid residues 64-89 and residues 562-588 of SEQ ID NO: 6 with a cysteine attached to the N-terminus. These peptides were conjugated to maleimide-activated KLH according to the manufacturer's protocol (Pierce Chemical Co., Rockford, Ill.). Rabbits were immunized (intramuscular injection) and subsequently boosted at regular intervals with 100 μg of KLH-peptide conjugate per injection. Anti-peptide antibodies were affinity purified on the corresponding peptide chromatographic column (Sulfolink™, Pierce Chemical Co., Rockford, Ill.) using Gentle Binding and Elution™ buffers (Pierce Chemical Co., Rockford, Ill.).

EXAMPLE 7

Immunoprecipitation and Immunoblotting

For immunoprecipitation, samples were extracted with TBS (20 mM Tris-HCl, 150 mM NaCl, pH 7.4) containing either 1% TX-100 or 1% Zwittergent 3-14 for at least 4 hours at 4° C. The extract was centrifuged at 100,000×g for 30 min, and the resultant supernatant solution was incubated for 2 hours with preimmune IgG covalently bound to Protein A agarose (Seize X™, Pierce Chemical Co., Rockford, Ill.). The nonbound fraction was recovered and incubated with peptide reactive antibody (=1.5 μM peptide preincubation)/Protein A agarose overnight with rocking at 4° C. The resulting immune complexes were washed 5 times. SDS-polyacrylamide electrophoresis was according to Laemmli (1970), *Nature* 227:680-5. Electrophoretically separated samples were transferred to nitrocellulose membranes according to Towbin et al. (1979), *Proc. Natl. Acad. Sci. USA* 76:4350-4, at 50V for 2 hours, 4° C. immunoblots were probed in TBST/2.5% nonfat milk with CatSper2 antibody (1:5000) or CatSper1 (1:2000) antibody. After incubation with the primary antibody, the blots were rinsed once with TBST/2.5% nonfat milk and washed with TBST (4 changes over 30 min). Blots were then incubated with secondary goat anti-rabbit IgG-HRP conjugate for 1 hour, washed with TBST (3 changes over 30 min), rinsed with TBS (3 times), and the signal detected with chemiluminescence (Pierce Chemical Co., Rockford, Ill.).

Both CatSper2 and CatSper1 are relatively insoluble when detergents other than SDS are used to extract epididymal sperm. The proteins were more easily solubilized from the testis with either 1% TX-100 or Zwittergent 3-14. While CatSper2 was immunoprecipitated from both of these detergent extracts with the C-terminus peptide antibody, CatSper1 remained in the soluble fraction. CatSper2 and CatSper1 could not be solubilized with CHAPS or other detergents.

EXAMPLE 8

Immunolocalization (Fluorescence)

Caudal epididymal sperm cells were spotted onto glass slides and are dried. The cells were fixed and permeabilized with ice-cold methanol for 2 min. The slides were rinsed in ethanol, air dried, and incubated with PBS/10% normal goat serum in CAS solution (Zymed Laboratories, Inc., South San Francisco, Calif.) for 30 min to block nonspecific binding. The slides were then incubated in primary antibody diluted in blocking solution (C-terminus antibody (1:5000); polyclonal antibody (1:1000)). Primary antibody was preincubated with either 20 μM competing peptide or a scrambled peptide prior to dilution in blocking solution to assess specific binding. Following the primary antibody incubation, the slides were washed with PBS (3×10 min), and incubated with goat anti-rabbit IgG-AlexaFluor-488 (Molecular Probes, Eugene, Oreg.) for 1 hr. After washing with PBS (3×10 min), the slides were mounted with Fluoromount G (Fisher Scientific, Pittsburgh, Pa.) for observation.

Two peptide-reactive antibodies were produced as described above. SDS polyacrylamide gel electrophores/immmmunoblots of mouse testis and crude sperm membrane SDS extracts with each affinity-purified antibody identified a 68,000 $M_r$ protein corresponding to the size predicted from the cDNA sequence. Similarly, a 68,000 $M_r$ protein was detected in rat epididymal sperm cell membranes. Indirect immunofluorescence was performed on methanol-fixed, permeabilized mouse contract epididymal sperm labeled with C-terminal peptide antibody. Bound antibody was detected with AlexaFluor-488 conjugated secondary antibody using phase contrast and epifluorescence microscopy. The CatSper2 protein localized to the flagellum. This signal was blocked by preincubation with a competing peptide, but not with a scrambled version of the peptide.

EXAMPLE 9

Fluorescence In Situ Hybridization

A mouse genomic clone was identified with the cDNA probe corresponding to nucleotides 113-531 of SEQ ID NO:

5. The BAC clone was labeled with digoxigenin dUTP by nick translation and used to probe normal metaphase chromosomes from mouse embryo fibroblast cells in 50% formamide, 10% dextran sulfate, and 2×SSC. Specific hybridization signals were detected with fluoresceinated anti-digoxigenin antibodies and the chromosomes counterstained with DAPI. A total of 80 metaphase cells were analyzed with specific labeling detected in each case (Incyte Genomics, Inc., Palo Alto, Calif.).

The CatSper2 gene is located on mouse chromosome 2 E5-F1. No reported mutations associated with male infertility are present in this region of the mouse genome. In the human, two genes with 70-75% identify to CatSper2 at the nucleotide level were identified on chromosome 15q13, a region that is syntenic with the mouse chromosome location of CatSper2. All three of the human testis clones described above appear to be transcribed from only one of these genes.

EXAMPLE 10

Electrophysiology

CatSper2, either alone, or together with CatSper1 and/or cyclic nucleotide gated channel submit (CNG4) were transfected into CHO-K1 and HEK-293 cells. Whole cell patch clamp recordings were done as previously described (Ren et al., (2001), supra). The pipette solution contained 120 mM Cs+, 60 mM glutamic acid, 20 mM TEA-Cl, 5 mM MgCl$_2$, 3 mM Mg-ATP, 10 mM EGTA, 10 mM HEPES and 5 mM D-glucose at pH 7.4. The bath contained 135 mM NaCl, 5 mM KCl, 10 mM CaCl$_2$, 10 mM Na-lactate, 10 mM Na-pyruvate, 10 mM glucose and 30 mM HEPES at pH 7.4.

In each case, an associated current elicited by changes in voltage, pH, osmolarity, and/or cyclic nucleotide concentration was not detected, indicating that CatSper2 alone does not form a functional ion channel in these cells. Similarly, heterologous expression of CatSper1 alone or in combination whit CNG channel β subunits failed to produce a functional ion channel (Ren et al. (2001), supra). As CatSper1 and CatSper2 are members of a unique ion channel family with overlapping expression patterns, their ability to associate to form a functional heterotetrameric channel was tested. Co-expression of these two proteins also failed to yield a functional channel.

EQUIVALENTS

While this invention has been particularly shown and described with references to certain embodiments thereof, it will be understood by those skilled in the art that various changes in form and details can be made therein without departing front the spirit and scope of the invention. Those skilled in the art will recognize, or be able to ascertain using no mote than routine experimentation, many equivalents to the specific embodiments of the invention described specifically herein. Such equivalents are intended to be encompassed in the scope of the invention.

SEQUENCE LISTING (human CatSper2 cDNA sequence - variant A2)
SEQ ID NO: 1

```
ATGGCCGCTT ACCAACAAGA AGAGCAGATG CAGCTTCCCC      0050
GAGCTGATGC

CATTCCTTCA CGTCTCATCG ATACTTTCTC TCTCATTGAG      0100
CATTTGCAAG

GCTTGAGCCA AGCTGTGCCG CGGCACACTA TCAGGGAGTT      0150
ACTTGATCCT

TCCCGCCAGA AGAAACTTGT ATTGGGAGAT CAACACCAGC      0200
TAGTGCGTTT

CTCTATAAAG CCTCAGCGTA TAGAACAGAT TTCACATGCC      0250
CAGAGGCTGT

TGAGCAGGCT TCATGTGCGC TGCAGTCAGA GGCCACCTCT      0300
TTCTTTGTGG

GCCGGATGGG TCCTTGAGTG TCCTCTCTTC AAAAACTTCA      0350
TCATCTTCCT

GGTCTTTTTG AATACGATCA TATTGATGGT TGAAATAGAA      0400
TTGCTGGAAT

CCACAAATAC CAAACTATGG CCATTGAAGC TGACCTTGGA      0450
GGTGGCAGCT

TGGTTTATCT TGCTTATTTT CATCCTGGAG ATCCTTCTTA      0500
AGTGGCTATC

CAACTTTTCT GTTTTCTGGA AGAGTGCCTG GAATGTCTTT      0550
GACTTTGTTG

TTACCATGTT GTCCCTGCTT CCCGAGGTTG TGGTATTGGT      0600
AGGGGTAACA

GGCCAATCGG TGTGGCTTCA GCTTCTGAGG ATCTGCCGGG      0650
TGCTGAGGTC

TCTCAAACTC CTTGCACAAT TCCGTCAAAT TCAAATTATT      0700
ATTTTGGTCC

TGGTCAGCGC CCTCAAGAGC ATGACCTTCC TCTTGATGTT      0750
GCTGCTCATC

TTCTTCTACA TTTTTGCTGT GACTCGTCTC TACGTCTTCT      0800
CAGAGTACAC

CCGTTCACCT CGTCACGACC TGGAGTACCA TGTGTTCTTC      0850
TCGCACCTCC

CGAATTCCCT GGTALCAGTG TTCATTCTCT TCACCTTGGA      0900
TCATTGGTAT

GCACTGCTTC AGGACGTCTG CAAGGTGCCT GAAGTCAGTC      0950
GCATCTTCAG

CAGCATCTAT TTCATCCTTT GGTTGTTGCT TGGCTCCATT      1000
ATCTTTCGAA

GTATCATAGT AGCCATGATG GTTACTAACT TTCAGAATAT      1050
CAGGAAAGAG

CTGAATGAGG AGATGGCGCG TCGGGAGGTT CAGCTCAAAG      1100
CTGACATGTT

CAAGCGGCAG ATCATCCAGA CGAGAAAAAA CATGTCACAT      1150
GAAGCACTGA

CGTCAACCCA TAGCAAAATA GAGGACAGAG GAGCTAGTCA      1200
ACAAAGGGAA

AGTTTGGACT TATCAGAAGT GTCTGAAGTA GAGTCTAATT      1250
ATGGTGCCAC

TGAAGAGGAT TTAATAACAT CTGCATCAAA AACAGAAGAG      1300
ACCTTGTCAA

AAAAGAGAGA GTACCAGTCT TCCTCCTGTG TCTCCTCCAC      1350
ATCCTCTTCC
```

| SEQUENCE LISTING | |
|---|---|
| TATTCTTCCT CTTCTGAATC CAGATTTTCT GAATCTATTG GTCGTTTGGA | 1400 |
| CTGGGAGACT CTTGTGCACG ALAATCTGCC CGGGCTAATG GAAATGGATC | 1450 |
| AGGATGACCG TGTTTGGCCC AGAGACTCAC TCTTCCGATA TTTTGAGTTG | 1500 |
| CTAGAAAAGC TTCAGTATAA CCTAGAGGAA CGTAAGAAGT TACAAGAGTT | 1550 |
| TGCAGTCCAG GCACTGATGA ACTTGGAAGA CAAGTAA | 1587 |

(human CatSper2 protein sequence - variant A2)
SEQ ID NO: 2

| | |
|---|---|
| MAAYQQEEQM QLPRADAIRS RLIDTFSLIE HLQGLSQAVP RHTIRELLDP | 0050 |
| SRQKKLVLGD QHQLVRESIK PQRIEQISHA QRLLSRLHVR CSQRPPLSLW | 0100 |
| AGWVIECPLF KNFITELVFL NTIILMVEIE LLESTNTKLW PLKLTLEVAA | 0150 |
| WFILLIFILE ILLKWLSNFS VFWKSAWNVF DFVVTMLSLL PEVTTLVGVT | 0200 |
| GQSVWLQLLR ICRVLRSLKL LAQFRQIQII ILVLVRALKS MTFLLMLLLI | 0250 |
| FFYIFAVTGV YVFSEYTRSP RQDLEYHVFF SDLPNSLVTV FILFTLDHWY | 0300 |
| ALLQDVWKVP EVSRIFSSIY FILWLLLGSI IFRSTIVAMM VTNFQNIRKE | 0350 |
| LNEEMARREV QLKADMFKRQ IIQRRKNMSE EALTSSHSKI EDRGASQQRE | 0400 |
| SLDLSEVSEV ESNYGATEED LITSASKTEE TLSKKREYQS SSCVSSTSSS | 0450 |
| YSSSSESRFS ESIGRLDWET LVHENLPGLM EMDQDDRVWP RDSLFRYFEL | 0500 |
| LEKLQYNLEE RKKLQEFAVQ ALMNLEDK | 0528 |

(human CatSper2 cDNA sequence - variant C1)
SEQ ID NO: 3

| | |
|---|---|
| ATGGCCGCTT ACCAACAAGA AGAGCAGATG CAGCTTCCCC GAGCTGATGC | 0050 |
| CATTCGTTCA CGTCTCATCG ATACTTTCTC TCTCATTGAG CATTTGCAAG | 0100 |
| GCTTGAGCCA AGCTGTGCCG CGGCACACTA TCAGGGAGTT ACTTGATCCT | 0150 |
| TCCCGCCAGA AGAAACTTGT ATTGGGAGAT CAACACGAGC TAGTGCGTTT | 0200 |
| CTCTATAAAG CCTCAGCGTA TAGAACAGAT TTCACATGCC CAGAGGCTGT | 0250 |
| TGAGCAGGCT TCATGTGCGC TGCAGTCAGA GGCCACCTCT TTCTTTGTGG | 0300 |
| GCCGGATGGG TCCTTGAGTG TCCTCTCTTC AAAAACTTCA TCATCTTCCT | 0350 |
| GGTCTTTTTG AATACGATCA TATTGATGGT TGAAATAGAA TTGCTGGAAT | 0400 |
| CCACAAATAC CAAACTATGG CCATTGAAGC TGACCTTGGA GGTGGCAGCT | 0450 |
| TGGTTTATCT TGCTTATTTT CATCCTGGAG ATCCTTCTTA AGTGGCTATC | 0500 |
| CAACTTTTCT GTTTTCTGGA AGAGTGCCTG GAATGTCTTT GACTTTGTTG | 0550 |
| TTACCATGTT GTCCCTGCTT CCCGAGGTTG TGCTATTGCT AGGGGTAACA | 0600 |
| GGCCAATCGG TGTGGCTTCA GCTTCTGAGG ATCTGCCGGG TGCTGAGGTC | 0650 |
| TCTCAAACTC CTTGCACAAT TCCGTCAAAT TCAAATTATT ATTTTGGTCC | 0700 |
| TGGTCAGGGC CCTCAAGAGC ATGACCTTCC TCTTGATGTT GCTGCTCATC | 0750 |
| TTCTTCTACA TTTTTCCTGT GACTGGTGTC TACGTCTTCT CAGAGTACAC | 0800 |
| CCGTTCACCT CGTCAGGACC TGGAGTACCA TGTGTTCTTC TCGGACCTCC | 0850 |
| CGAATTCCCT GGTAACAGTG TTCATTCTCT TCACCTTGGA TCATTGGTAT | 0900 |
| GCACTGGTTC AGGACGTCTG GAAGGTGCCT GAAGTCAGTC GCATCTTCAG | 0950 |
| CAGCATCTAT TTCATCCTTT GGTTGTTGCT TGGCTCCATT ATCTTTCGAA | 1000 |
| GTATCATAGT AGCCATGATG GTTACTAACT TTCAGAATAT CAGGAAAGAG | 1050 |
| CTGAATGAGG AGATGGCGCG TCGGGAGGTT CAGCTCAAAG CTGACATGTT | 1100 |
| CAAGCGGCAG ATCATCCAGA GGAGAAAAAA GATGTCACAT GAAGCACTGA | 1150 |
| CGTCAAGCCA TAGCAAAATA GAGGACAGGT CGTTTGGACT GGGAGACTCT | 1200 |
| TGTGCACGAA AATCTGCCCG GGCTAATGGA AATGGATCAG GATGA | 1245 |

(human CatSper2 protein sequence - variant C1)
SEQ ID NO: 4

| | |
|---|---|
| MAAYQQEFQM QLPRADAIRS RLIDTFSLIE HLQGLSQAVP RHTIRELLDP | 0050 |
| SRQKKLVIGD QHQLVRFSIK PQRIEQISHA QRLLSRLHVR CSQRPPLSLW | 0100 |
| AGWVLECPLF KNFIIFLVFL NTIILMVEIE LLESTNTKLV PLKLTLEVAA | 0150 |
| WFILLIFILE ILLKWLSNFS VFWKSAWNVF DFVVTMLSLL PEVVVLVGVT | 0200 |
| GQSVWLQLLR ICRVLRSLKL LAQFRQIQII ILVLVRALKS MTFLLMLLLI | 0250 |
| FFYIFAVTGV YVFSEYTREP RQDLEYHVFF SDLPNSLVTV FILFTLDHWY | 0300 |
| ALLQDVWKVP EVSRIFSSIY FILWLLLGSI IFRSIIVAMM VTNFQNIRKE | 0350 |
| LNEEMARREV QLKADMFKRQ IIORRKNMSH EALTSSHSKI EDRSFGLQDS | 0400 |
| CARKSARANG NGSG | 0414 |

| SEQUENCE LISTING |
|---|
| (murine CatSper2 cDNA sequence) SEQ ID NO: 5 |
| ATGGCACAAG AACAAGGACA TTTCCAGCTG CTCAGAGCTG     0050<br>ATGCTATCCG |
| TTCAAAGCTC ATTGACACTT TCTCGCTCAT AGAGCATTTG     0100<br>CAGGGCTTGA |
| GCCAAGCCGT ACCAAGGCAC ACTCTCCGGG AGATACTTGA     0150<br>TCCTGCTTAC |
| CAGCAGALAC TCATGTGAGG AGATCAGGAG CAGCTAGTGC     0200<br>GCTTCTCCAT |
| AAAGCCTCGG CGAATGGGGC ACATCACACA CTCGCGGCGG     0250<br>TTGCTGAGCA |
| GGGTTCGCGT GCGGTGCAGT CGAATGCCCC CTCTTTCCTT     0300<br>GTGGGCTGGA |
| TGGGTCCTTG ATAGTTCTGT CTTCTCGAAA TTCATCATCT     0350<br>CCCTCATCTT |
| TCTGAACACC TTTGTGCTGA TGGTTGAAAT AGAATTGATG     0400<br>GAATCCACAA |
| ATACTGCTCT GTGGCCAGTG AAGCTGGCTT TGGAGGTGGC     0450<br>AGATTGGTTC |
| ATCTTGCTTA GCTTCATTGT AGAGATACTT CTAATGTGGT     0500<br>TGGCCAGTTT |
| TTCTCTCTTC TGGAAGGATG CCTGGAATGT CTTTGACTTT     0550<br>TTTGTTACCT |
| TGTTGTCTCT GCTTCCTGAG TTAGTAGTGC TGTTAGGAGT     0600<br>CCCAGCACAC |
| TCTGTGTGGC TCCAGCTGGT GAGGGTCTGT CGGGTGCTGA     0650<br>GGTCTCTCAA |
| ACTGTTTGCA CGATTCCGTC AAATTAAACT TATTCTTTTG     0700<br>GGTCTGGTCA |
| GGGGCCTGAA GAGCATGACC TTCCTCTTGA TGTTGCTGCT     0750<br>TATCTTCTTC |
| TACATTTTTG CTCTGACTGC TGTCTACTTC TTCAGAGAAT     0800<br>ATTCCCGATC |
| AACTATCGAG GGCCTGGAGT ACAACATGTT CTTCTCGGAC     0850<br>CTACTAAATT |
| CACTGGTGAC AGTGTTCATC CTCTTCACCT TGGATCATTG     0900<br>GTATGCAGTA |
| CTTCAGAATA TCTGGAAGGT GCCAGAATCT AGCCGTGTCT     0950<br>TTAGGAGCAT |
| CTATGTTATC CTTTGGTTGC TGCTTGGCTC CATAATCTTT     1000<br>CGAAATATCA |
| TAATAGCCAT GATGGTTACT AACTTTCAGA ATATCAGAAG     1050<br>TGAGCTGAGT |
| GAGGAGATGA GCCACCTGGA GGTTCAGTAT AAAGCTGACA     1100<br>TGTTCAAGCA |
| ACAGATTATC CAGAGGAGAC AGCACTCTGA ATCACTAAGA     1150<br>GGGACCAGTC |
| TTGGAAAGGT CTCCGAAGAC ATAATAGAAA CTTCTGATGC     1200<br>TAGTGATGAT |
| GATGACGATG ACGACGATGA TGACGACGAC GATGATGATG     1250<br>ATGATGATGA |
| CAAAAGCGAT GCTACTCAAA GCGATGGCGA GGAAAGCGAT     1300<br>AGTGAGAATA |
| GTGAGAGTGA GAATAGCGAG AGCGAGAAAA TTGATCCTGA     1350<br>GAAAGACTAT |
| GCCAAGAAAA GCTATCCTGA GAAAAGCCAT CCTGAGZAAA     1400<br>GCTATCCTGA |
| GAAAAGCCAT CCTGAGAAAA GCTATCCTGA GAAAAGCCAT     1450<br>CCTGAGAAAA |
| GCTATGATGA ACAGGCTGAA GCTGAAAAAG TAALAGAAGA     1500<br>GTCAAAAGAA |
| AAAGCCTACC CAGTTTCCCA TTCAATCTCG TCCCATGGCT     1550<br>CCATTGCAGC |
| CGATAGTGCT TTCCTTGAAA ACCTGGACTG GGAGACCCTT     1600<br>GTGCATGAGA |
| ACCTGCCTGG GCTAATGGAC ATGGATCAGG ATGACCGCAT     1650<br>TGTCTGGCCC |
| AGAGACTCAC TCTTCCGATA TTTCGAGTTA CTGGAAAAGC     1700<br>TTCAGTATAA |
| CCTAGAAGAG CGCAAGAAGT TACAAGAATT TGCAGTCCAG     1750<br>GCCCTGATGA |
| GTTTTGAAGA CAAGTGA                              1767 |
| (murine CatSper2 protein sequence) SEQ ID NO: 6 |
| MAQEQGHFQL LRADAIRSKL IDTFSLIEHL QGLSQAVPRH     0050<br>TLREILDPAY |
| QQKLMSGDOE QLVRFSIKPR RMGHITHSRR LLSEIRVRCS     0100<br>RMPPLSLWAG |
| WVLDSSVFSK FIISLIFLNT FVLMVEIELM ESTNTALWPV     0150<br>KLALEVADWF |
| ILLSFIVEIL LMWLASFSLF WKDAWNVEDF FVTLLSLLPE     0200<br>LVVLLGVPAH |
| SVWLQLLRVC RVIRSLKLFA RFRQIKVILL AINRALKSMT     0250<br>FLLMLLLIFF |
| YIFAVTGVYF FREYSRSTIE GLEYNMFFSD LLNSLVTVFI     0300<br>LFTLDHWYAV |
| LQNIWKVPES SRVFSSIYVI LWLLLGSIIF RNITIAMMVT     0350<br>NFQNIRSELS |
| EEMSHLEVQY KADMFKQQII QRRQHSESLR GTSLGKVSED     0400<br>IIETSDASDD |
| DDDDDDDDD DDDDDDDKSD ATESDGEESD SENSESENSE     0450<br>SEKIDPEKDY |
| AKKSYPEKSH PEKSYPEKSH PEKSYPEKSH PEKSYDEQAE     0500<br>AEKVKEESKE |
| KAYPVSHSIS SHOSIAADTA FLENLDWETL VHENLPGLMD     0550<br>MDQDDRIVWP |
| RDSLFRYFEL LEKLQYWLEE RKKLQUFAVQ ALMSFEDK       0588 |

We claim:

1. A method of selecting a compound having potential contraceptive activity, the method comprising:
   (a) contacting a candidate compound with a sperm cell expressing a protein having at least 95% amino acid sequence identity with the CatSper2 protein of SEQ ID NO: 2 or 6, wherein the nucleotide sequence is derived from SEQ ID NO: 1 or 5, or variants thereof that differ from SEQ ID NO: 1 or 5 by substitution of at least one synonymous codon, and wherein the protein has CatSper2 activity;
   (b) measuring an indicator of CatSper2 activity in the cell, wherein the indicator is a measure of sperm motility;
   (c) determining whether said candidate compound caused a decrease in CatSper2 activity in the cell relative to CatSper2 activity prior to contact with the candidate compound; and
   (d) toxicity profiling the candidate compound; and
   (e) selecting said candidate compound that causes a decrease in CatSper2 activity as having potential contraceptive activity.

2. A method of selecting a compound having potential contraceptive activity, the method comprising:
   (a) contacting normal sperm with a candidate compound previously identified as causing a decrease in an indicator of CatSper2 activity in a cell, wherein the indicator is a measure of sperm motility, the protein having at least 95% amino acid sequence identity with the CatSper2 protein of SEQ ID NO: 2 or 6, wherein the nucleotide sequence is derived from SEQ ID NO: 1 or 5, or variants thereof that differ from SEQ ID NO: 1 or 5 by substitution of at least one synonymous codon, and wherein the protein has CatSper2 activity;
   (b) assaying for a decrease in sperm motility relative to sperm motility in the cell prior to contact with the candidate compound;
   (c) toxicity profiling the candidate compound; and
   (d) selecting said candidate compound that causes a decrease in sperm motility as having potential contraceptive activity.

3. The method of claim 2, wherein said candidate compound was previously identified as causing a decrease in CatSper2 activity in a cell by the steps comprising:
   (1) contacting a sperm cell expressing a CatSper2 protein with at least one candidate compound from a library, the protein having at least 95% amino acid sequence identity with the CatSper2 protein of SEQ ID NO: 2 or 6, wherein the nucleotide sequence is derived from SEQ ID NO: 1 or 5, or variants thereof that differ from SEQ ID NO: 1 or 5 by substitution of at least one synonymous codon, and wherein the protein has CatSper2 activity;
   (2) measuring an indicator of CatSper2 activity in the cell, wherein the indicator is a measure of sperm motility;
   (3) determining whether the candidate compound caused a decrease in CatSper2 activity in the cell relative to CatSper2 activity prior to contact with the candidate compound;
   (4) toxicity profiling the candidate compound; and
   (5) identifying the candidate compound from the library as causing a decrease in CatSper2 activity in the cell.

4. The method of claim 2, wherein said candidate compound was previously identified as causing a decrease in CatSper2 activity in a cell by the steps comprising:
   (1) contacting a sperm cell expressing a CatSper2 protein with at least one candidate compound from a library, the protein having at least 95% amino acid sequence identity with the CatSper2 protein of SEQ ID NO: 2 or 6, wherein the nucleotide sequence is derived from SEQ ID NO: 1 or 5, or variants thereof that differ from SEQ ID NO: 1 or 5 by substitution of at least one synonymous codon, and wherein the protein has CatSper2 activity;
   (2) measuring an indicator of CatSper2 activity in the cell, wherein the indicator is a measure of sperm motility;
   (3) determining whether the candidate compound caused a decrease in CatSper2 activity in the cell relative to CatSper2 activity prior to contact with the candidate compound;
   (4) toxicity profiling the candidate compound; and
   (5) identifying the candidate compound from the library as causing a decrease in CatSper2 activity in the cell.

5. A method of selecting a compound having potential contraceptive activity, the method comprising:
   (a) contacting a candidate compound with a sperm cell expressing a CatSper2 protein, the CatSper2 protein having at least 95% amino acid sequence identity with the CatSper2 protein of SEQ ID NO: 2 or 6, wherein the nucleotide sequence is derived from SEQ ID NO: 1 or 5, or variants thereof that differ from SEQ ID NO: 1 or 5 by substitution of at least one synonymous codon, and wherein the protein has CatSper2 activity;
   (b) measuring an indicator of CatSper2 activity in the cell, wherein the indicator is a measure of sperm motility;
   (c) determining whether said candidate compound caused a decrease in CatSper2 activity in the cell relative to CatSper2 activity prior to contact with the candidate compound;
   (d) toxicity profiling the candidate compound; and
   (e) selecting said candidate compound that causes a decrease in CatSper2 activity as having potential contraceptive activity.

6. The method as in claim 5, wherein toxicity profiling is performed in an animal.

7. The method as in claim 6, wherein toxicity profiling is performed by monitoring the animal for adverse changes in at least one of immune function, kidney function, liver function, and cardiac function.

* * * * *

UNITED STATES PATENT AND TRADEMARK OFFICE
CERTIFICATE OF CORRECTION

PATENT NO. : 9,618,521 B2
APPLICATION NO. : 14/249990
DATED : April 11, 2017
INVENTOR(S) : Dejian Ren et al.

Page 1 of 1

It is certified that error appears in the above-identified patent and that said Letters Patent is hereby corrected as shown below:

In the Specification

At Column 1, Line number 18, should read:
This invention was made with government support under Grant number HD036022 awarded by The National Institutes of Health. The government has certain rights in the invention.

Signed and Sealed this
Fifth Day of January, 2021

Andrei Iancu
*Director of the United States Patent and Trademark Office*

SEQUENCE LISTING

<160> NUMBER OF SEQ ID NOS: 7

<210> SEQ ID NO 1
<211> LENGTH: 1587
<212> TYPE: DNA
<213> ORGANISM: Homo sapiens

<400> SEQUENCE: 1

| | | | | | |
|---|---|---|---|---|---|
| atggccgctt | accaacaaga | agagcagatg | cagcttcccc | gagctgatgc | cattcgttca | 60 |
| cgtctcatcg | atactttctc | tctcattgag | catttgcaag | gcttgagcca | agctgtgccg | 120 |
| cggcacacta | tcagggagtt | acttgatcct | tcccgccaga | agaaacttgt | attgggagat | 180 |
| caacaccagc | tagtgcgttt | ctctataaag | cctcagcgta | tagaacagat | ttcacatgcc | 240 |
| cagaggctgt | tgagcaggct | tcatgtgcgc | tgcagtcaga | ggccacctct | ttctttgtgg | 300 |
| gccggatggg | tccttgagtg | tcctctcttc | aaaaacttca | tcatcttcct | ggtcttttg | 360 |
| aatacgatca | tattgatggt | tgaaatagaa | ttgctggaat | ccacaaatac | caaactatgg | 420 |
| ccattgaagc | tgaccttgga | ggtggcagct | tggtttatct | tgcttatttt | catcctggag | 480 |
| atccttctta | agtggctatc | caactttct | gttttctgga | agagtgcctg | gaatgtcttt | 540 |
| gactttgttg | ttaccatgtt | gtccctgctt | cccgaggttg | tggtattggt | aggggtaaca | 600 |
| ggccaatcgg | tgtggcttca | gcttctgagg | atctgccggg | tgctgaggtc | tctcaaactc | 660 |
| cttgcacaat | tccgtcaaat | tcaaattatt | atttggtcc | tggtcagggc | cctcaagagc | 720 |
| atgaccttcc | tcttgatgtt | gctgctcatc | ttcttctaca | ttttgctgt | gactggtgtc | 780 |
| tacgtcttct | cagagtacac | ccgttcacct | cgtcaggacc | tggagtacca | tgtgttcttc | 840 |
| tcggacctcc | cgaattccct | ggtaacagtg | ttcattctct | tcaccttgga | tcattggtat | 900 |
| gcactgcttc | aggacgtctg | gaaggtgcct | gaagtcagtc | gcatcttcag | cagcatctat | 960 |
| ttcatccttt | ggttgttgct | tggctccatt | atctttcgaa | gtatcatagt | agccatgatg | 1020 |
| gttactaact | ttcagaatat | caggaaagag | ctgaatgagg | agatggcgcg | tcgggaggtt | 1080 |
| cagctcaaag | ctgacatgtt | caagcggcag | atcatccaga | ggagaaaaaa | catgtcacat | 1140 |
| gaagcactga | cgtcaagcca | tagcaaaata | gaggacagag | gagctagtca | acaaagggaa | 1200 |
| agtttggact | tatcagaagt | gtctgaagta | gagtctaatt | atggtgccac | tgaagaggat | 1260 |
| ttaataacat | ctgcatcaaa | aacagaagag | accttgtcaa | aaagagaga | gtaccagtct | 1320 |
| tcctcctgtg | tctcctccac | atcctcttcc | tattcttcct | cttctgaatc | cagatttct | 1380 |
| gaatctattg | gtcgtttgga | ctgggagact | cttgtgcacg | aaaatctgcc | cgggctaatg | 1440 |
| gaaatggatc | aggatgaccg | tgtttggccc | agagactcac | tcttccgata | ttttgagttg | 1500 |
| ctagaaaagc | ttcagtataa | cctagaggaa | cgtaagaagt | tacaagagtt | tgcagtgcag | 1560 |
| gcactgatga | acttggaaga | caagtaa | | | | 1587 |

<210> SEQ ID NO 2
<211> LENGTH: 528
<212> TYPE: PRT
<213> ORGANISM: Homo sapiens

<400> SEQUENCE: 2

Met Ala Ala Tyr Gln Gln Glu Glu Gln Met Gln Leu Pro Arg Ala Asp
  1               5                  10                  15

Ala Ile Arg Ser Arg Leu Ile Asp Thr Phe Ser Leu Ile Glu His Leu
             20                  25                  30

Gln Gly Leu Ser Gln Ala Val Pro Arg His Thr Ile Arg Glu Leu Leu

-continued

```
                 35                  40                  45
Asp Pro Ser Arg Gln Lys Lys Leu Val Leu Gly Asp Gln His Gln Leu
 50                  55                  60
Val Arg Phe Ser Ile Lys Pro Gln Arg Ile Glu Gln Ile Ser His Ala
 65                  70                  75                  80
Gln Arg Leu Leu Ser Arg Leu His Val Arg Cys Ser Gln Arg Pro Pro
                 85                  90                  95
Leu Ser Leu Trp Ala Gly Trp Val Leu Glu Cys Pro Leu Phe Lys Asn
                100                 105                 110
Phe Ile Ile Phe Leu Val Phe Leu Asn Thr Ile Ile Leu Met Val Glu
                115                 120                 125
Ile Glu Leu Leu Glu Ser Thr Asn Thr Lys Leu Trp Pro Leu Lys Leu
                130                 135                 140
Thr Leu Glu Val Ala Ala Trp Phe Ile Leu Ile Phe Ile Leu Glu
145                 150                 155                 160
Ile Leu Leu Lys Trp Leu Ser Asn Phe Ser Val Phe Trp Lys Ser Ala
                165                 170                 175
Trp Asn Val Phe Asp Phe Val Val Thr Met Leu Ser Leu Leu Pro Glu
                180                 185                 190
Val Val Leu Val Gly Val Thr Gly Gln Ser Val Trp Leu Gln Leu
                195                 200                 205
Leu Arg Ile Cys Arg Val Leu Arg Ser Leu Lys Leu Leu Ala Gln Phe
                210                 215                 220
Arg Gln Ile Gln Ile Ile Leu Val Leu Val Arg Ala Leu Lys Ser
225                 230                 235                 240
Met Thr Phe Leu Leu Met Leu Leu Ile Phe Phe Tyr Ile Phe Ala
                245                 250                 255
Val Thr Gly Val Tyr Val Phe Ser Glu Tyr Thr Arg Ser Pro Arg Gln
                260                 265                 270
Asp Leu Glu Tyr His Val Phe Phe Ser Asp Leu Pro Asn Ser Leu Val
                275                 280                 285
Thr Val Phe Ile Leu Phe Thr Leu Asp His Trp Tyr Ala Leu Leu Gln
                290                 295                 300
Asp Val Trp Lys Val Pro Glu Val Ser Arg Ile Phe Ser Ser Ile Tyr
305                 310                 315                 320
Phe Ile Leu Trp Leu Leu Leu Gly Ser Ile Phe Arg Ser Ile Ile
                325                 330                 335
Val Ala Met Met Val Thr Asn Phe Gln Asn Ile Arg Lys Glu Leu Asn
                340                 345                 350
Glu Glu Met Ala Arg Arg Glu Val Gln Leu Lys Ala Asp Met Phe Lys
                355                 360                 365
Arg Gln Ile Ile Gln Arg Arg Lys Asn Met Ser His Glu Ala Leu Thr
                370                 375                 380
Ser Ser His Ser Lys Ile Glu Asp Arg Gly Ala Ser Gln Gln Arg Glu
385                 390                 395                 400
Ser Leu Asp Leu Ser Glu Val Ser Glu Val Glu Ser Asn Tyr Gly Ala
                405                 410                 415
Thr Glu Glu Asp Leu Ile Thr Ser Ala Ser Lys Thr Glu Thr Leu
                420                 425                 430
Ser Lys Lys Arg Glu Tyr Gln Ser Ser Cys Val Ser Ser Thr Ser
                435                 440                 445
Ser Ser Tyr Ser Ser Ser Glu Ser Arg Phe Ser Glu Ser Ile Gly
                450                 455                 460
```

Arg Leu Asp Trp Glu Thr Leu Val His Glu Asn Leu Pro Gly Leu Met
465                 470                 475                 480

Glu Met Asp Gln Asp Asp Arg Val Trp Pro Arg Asp Ser Leu Phe Arg
                485                 490                 495

Tyr Phe Glu Leu Leu Glu Lys Leu Gln Tyr Asn Leu Glu Glu Arg Lys
                500                 505                 510

Lys Leu Gln Glu Phe Ala Val Gln Ala Leu Met Asn Leu Glu Asp Lys
        515                 520                 525

<210> SEQ ID NO 3
<211> LENGTH: 1245
<212> TYPE: DNA
<213> ORGANISM: Homo sapiens

<400> SEQUENCE: 3

```
atggccgctt accaacaaga gagcagatg  cagcttcccc gagctgatgc cattcgttca      60
cgtctcatcg atactttctc tctcattgag catttgcaag gcttgagcca agctgtgccg     120
cggcacacta tcagggagtt acttgatcct ccccgccaga gaaacttgt  attgggagat    180 caacaccagc tagtgcgttt ctctataaag cctcagcgta tagaacagat ttcacatgcc     240
cagaggctgt tgagcaggct tcatgtgcgc tgcagtcaga ggccacctct ttctttgtgg     300
gccggatggg tccttgagtg tcctctcttc aaaaacttca tcatcttcct ggtcttttg     360 aatacgatca tattgatggt tgaaatagaa ttgctggaat ccacaaatac caaactatgg    420
ccattgaagc tgaccttgga ggtggcagct tggtttatct tgcttatttt catcctggag     480
atccttctta agtggctatc caactttct  gttttctgga gagtgcctg  gaatgtcttt     540 gactttgttg ttaccatgtt gtccctgctt cccgaggttg tggtattggt aggggtaaca     600
ggccaatcgg tgtggcttca gcttctgagg atctgccggg tgctgaggtc tctcaaactc     660
cttgcacaat tccgtcaaat tcaaattatt attttggtcc tggtcagggc cctcaagagc     720
atgaccttcc tcttgatgtt gctgctcatc ttcttctaca ttttttgctgt gactggtgtc    780 tacgtcttct cagagtacac ccgttcacct cgtcaggacc tggagtacca tgtgttcttc     840
tcggacctcc cgaattccct ggtaacagtg ttcattctct tcaccttgga tcattggtat     900
gcactgcttc aggacgtctg gaaggtgcct gaagtcagtc gcatcttcag cagcatctat     960
ttcatccttt ggttgttgct tggctccatt atctttcgaa gtatcatagt agccatgatg    1020
gttactaact ttcagaatat caggaaagag ctgaatgagg agatggcgcg tcgggaggtt    1080
cagctcaaag ctgacatgtt caagcggcag atcatccaga ggagaaaaaa catgtcacat    1140
gaagcactga cgtcaagcca tagcaaaata gaggacaggt cgtttggact gggagactct    1200
tgtgcacgaa atctgcccg  ggctaatgga aatggatcag atga                     1245
```

<210> SEQ ID NO 4
<211> LENGTH: 414
<212> TYPE: PRT
<213> ORGANISM: Homo sapiens

<400> SEQUENCE: 4

Met Ala Ala Tyr Gln Gln Glu Glu Gln Met Gln Leu Pro Arg Ala Asp
1               5                   10                  15

Ala Ile Arg Ser Arg Leu Ile Asp Thr Phe Ser Leu Ile Glu His Leu
                20                  25                  30

Gln Gly Leu Ser Gln Ala Val Pro Arg His Thr Ile Arg Glu Leu Leu
        35                  40                  45

```
Asp Pro Ser Arg Gln Lys Leu Val Leu Gly Asp Gln His Gln Leu
 50                  55                  60

Val Arg Phe Ser Ile Lys Pro Gln Arg Ile Glu Gln Ile Ser His Ala
 65                  70                  75                  80

Gln Arg Leu Leu Ser Arg Leu His Val Arg Cys Ser Gln Arg Pro Pro
                 85                  90                  95

Leu Ser Leu Trp Ala Gly Trp Val Leu Glu Cys Pro Leu Phe Lys Asn
            100                 105                 110

Phe Ile Ile Phe Leu Val Phe Leu Asn Thr Ile Ile Leu Met Val Glu
        115                 120                 125

Ile Glu Leu Leu Glu Ser Thr Asn Thr Lys Leu Trp Pro Leu Lys Leu
    130                 135                 140

Thr Leu Glu Val Ala Ala Trp Phe Ile Leu Leu Ile Phe Ile Leu Glu
145                 150                 155                 160

Ile Leu Leu Lys Trp Leu Ser Asn Phe Ser Val Phe Trp Lys Ser Ala
                165                 170                 175

Trp Asn Val Phe Asp Phe Val Val Thr Met Leu Ser Leu Leu Pro Glu
            180                 185                 190

Val Val Val Leu Val Gly Val Thr Gly Gln Ser Val Trp Leu Gln Leu
        195                 200                 205

Leu Arg Ile Cys Arg Val Leu Arg Ser Leu Lys Leu Leu Ala Gln Phe
    210                 215                 220

Arg Gln Ile Gln Ile Ile Leu Val Leu Val Arg Ala Leu Lys Ser
225                 230                 235                 240

Met Thr Phe Leu Leu Met Leu Leu Ile Phe Phe Tyr Ile Phe Ala
                245                 250                 255

Val Thr Gly Val Tyr Val Phe Ser Glu Tyr Thr Arg Ser Pro Arg Gln
            260                 265                 270

Asp Leu Glu Tyr His Val Phe Phe Ser Asp Leu Pro Asn Ser Leu Val
        275                 280                 285

Thr Val Phe Ile Leu Phe Thr Leu Asp His Trp Tyr Ala Leu Leu Gln
    290                 295                 300

Asp Val Trp Lys Val Pro Glu Val Ser Arg Ile Phe Ser Ser Ile Tyr
305                 310                 315                 320

Phe Ile Leu Trp Leu Leu Leu Gly Ser Ile Ile Phe Arg Ser Ile Ile
                325                 330                 335

Val Ala Met Met Val Thr Asn Phe Gln Asn Ile Arg Lys Glu Leu Asn
            340                 345                 350

Glu Glu Met Ala Arg Arg Glu Val Gln Leu Lys Ala Asp Met Phe Lys
        355                 360                 365

Arg Gln Ile Ile Gln Arg Lys Asn Met Ser His Glu Ala Leu Thr
    370                 375                 380

Ser Ser His Ser Lys Ile Glu Asp Arg Ser Phe Gly Leu Gly Asp Ser
385                 390                 395                 400

Cys Ala Arg Lys Ser Ala Arg Ala Asn Gly Asn Gly Ser Gly
                405                 410
```

<210> SEQ ID NO 5
<211> LENGTH: 1767
<212> TYPE: DNA
<213> ORGANISM: Mus musculus

<400> SEQUENCE: 5
atggcacaag aacaaggaca tttccagctg ctcagagctg atgctatccg ttcaaagctc        60

```
attgacactt tctcgctcat agagcatttg cagggcttga gccaagccgt accaaggcac    120
actctccggg agatacttga tcctgcttac cagcagaaac tcatgtcagg agatcaggag    180
cagctagtgc gcttctccat aaagcctcgg cgaatggggc acatcacaca ctcgcggcgg    240
ttgctgagca ggcttcgcgt gcggtgcagt cgaatgcccc ctctttcctt gtgggctgga    300
tgggtccttg atagttctgt cttctcgaaa ttcatcatct ccctcatctt tctgaacacc    360
tttgtgctga tggttgaaat agaattgatg gaatccacaa atactgctct gtggccagtg    420
aagctggctt tggaggtggc agattggttc atcttgctta gcttcattgt agagatactt    480
ctaatgtggt tggccagttt ttctctcttc tggaaggatg cctggaatgt ctttgacttt    540
tttgttacct tgttgtctct gcttcctgag ttagtagtgc tgttaggagt cccagcacac    600
tctgtgtggc tccagctgct gagggtctgt cgggtgctga ggtctctcaa actgtttgca    660
cgattccgtc aaattaaagt tattcttttg gctctggtca gggccctgaa gagcatgacg    720
ttcctcttga tgttgctgct tatcttcttc tacattttg ctgtgactgg tgtctacttc    780
ttcagagaat attcccgatc aactatcgag ggcctggagt acaacatgtt cttctcggac    840
ctactaaatt cactggtgac agtgttcatc ctcttcacct tggatcattg gtatgcagta    900
cttcagaata tctggaaggt gccagaatct agccgtgtct ttagcagcat ctatgttatc    960
ctttggttgc tgcttggctc cataatcttt cgaaatatca aatagccat gatggttact    1020 aactttcaga atatcagaag tgagctgagt gaggagatga gccacctgga ggttcagtat    1080
aaagctgaca tgttcaagca acagattatc cagaggagac agcactctga atcactaaga    1140
gggaccagtc ttggaaaggt ctccgaagac ataatagaaa cttctgatgc tagtgatgat    1200
gatgacgatg acgacgatga tgacgacgac gatgatgatg atgatgatga caaaagcgat    1260
gctactgaaa gcgatggcga ggaaagcgat agtgagaata gtgagagtga aatagcgag    1320 agcgagaaaa ttgatcctga aaagactat gccaagaaaa gctatcctga aaaagccat    1380 cctgagaaaa gctatcctga aaaagccat cctgagaaaa gctatcctga aaaagccat    1440 cctgagaaaa gctatgatga acaggctgaa gctgaaaaag taaaagaaga gtcaaaagaa    1500
aaagcctacc cagtttccca ttcaatctcg tcccatggct ccattgcagc cgatactgct    1560
ttccttgaaa acctggactg ggagacccctt gtgcatgaga acctgcctgg gctaatggac    1620
atggatcagg atgaccgcat tgtctggccc agagactcac tcttccgata tttcgagtta    1680
ctggaaaagc ttcagtataa cctagaagag cgcaagaagt tacaagaatt tgcagtccag    1740
gccctgatga gttttgaaga caagtga                                         1767

<210> SEQ ID NO 6
<211> LENGTH: 588
<212> TYPE: PRT
<213> ORGANISM: Mus musculus

<400> SEQUENCE: 6

Met Ala Gln Glu Gln Gly His Phe Gln Leu Leu Arg Ala Asp Ala Ile
  1               5                  10                  15

Arg Ser Lys Leu Ile Asp Thr Phe Ser Leu Ile Glu His Leu Gln Gly
             20                  25                  30

Leu Ser Gln Ala Val Pro Arg His Thr Leu Arg Glu Ile Leu Asp Pro
         35                  40                  45

Ala Tyr Gln Gln Lys Leu Met Ser Gly Asp Gln Glu Gln Leu Val Arg
     50                  55                  60
```

-continued

Phe Ser Ile Lys Pro Arg Arg Met Gly His Ile Thr His Ser Arg Arg
65                  70                  75                  80

Leu Leu Ser Arg Leu Arg Val Arg Cys Ser Arg Met Pro Pro Leu Ser
            85                  90                  95

Leu Trp Ala Gly Trp Val Leu Asp Ser Ser Val Phe Ser Lys Phe Ile
        100                 105                 110

Ile Ser Leu Ile Phe Leu Asn Thr Phe Val Leu Met Val Glu Ile Glu
        115                 120                 125

Leu Met Glu Ser Thr Asn Thr Ala Leu Trp Pro Val Lys Leu Ala Leu
        130                 135                 140

Glu Val Ala Asp Trp Phe Ile Leu Leu Ser Phe Ile Val Glu Ile Leu
145                 150                 155                 160

Leu Met Trp Leu Ala Ser Phe Ser Leu Phe Trp Lys Asp Ala Trp Asn
            165                 170                 175

Val Phe Asp Phe Phe Val Thr Leu Leu Ser Leu Leu Pro Glu Leu Val
            180                 185                 190

Val Leu Leu Gly Val Pro Ala His Ser Val Trp Leu Gln Leu Leu Arg
            195                 200                 205

Val Cys Arg Val Leu Arg Ser Leu Lys Leu Phe Ala Arg Phe Arg Gln
210                 215                 220

Ile Lys Val Ile Leu Leu Ala Leu Val Arg Ala Leu Lys Ser Met Thr
225                 230                 235                 240

Phe Leu Leu Met Leu Leu Ile Phe Phe Tyr Ile Phe Ala Val Thr
                245                 250                 255

Gly Val Tyr Phe Phe Arg Glu Tyr Ser Arg Ser Thr Ile Glu Gly Leu
            260                 265                 270

Glu Tyr Asn Met Phe Phe Ser Asp Leu Leu Asn Ser Leu Val Thr Val
            275                 280                 285

Phe Ile Leu Phe Thr Leu Asp His Trp Tyr Ala Val Leu Gln Asn Ile
            290                 295                 300

Trp Lys Val Pro Glu Ser Ser Arg Val Phe Ser Ser Ile Tyr Val Ile
305                 310                 315                 320

Leu Trp Leu Leu Leu Gly Ser Ile Ile Phe Arg Asn Ile Ile Ala
            325                 330                 335

Met Met Val Thr Asn Phe Gln Asn Ile Arg Ser Glu Leu Ser Glu Glu
            340                 345                 350

Met Ser His Leu Glu Val Gln Tyr Lys Ala Asp Met Phe Lys Gln Gln
            355                 360                 365

Ile Ile Gln Arg Arg Gln His Ser Glu Ser Leu Arg Gly Thr Ser Leu
            370                 375                 380

Gly Lys Val Ser Glu Asp Ile Ile Glu Thr Ser Asp Ala Ser Asp Asp
385                 390                 395                 400

Asp Asp Asp Asp Asp Asp Asp Asp Asp Asp Asp Asp Asp Asp Asp
                405                 410                 415

Asp Lys Ser Asp Ala Thr Glu Ser Asp Gly Glu Glu Ser Asp Ser Glu
            420                 425                 430

Asn Ser Glu Ser Glu Asn Ser Glu Ser Glu Lys Ile Asp Pro Glu Lys
            435                 440                 445

Asp Tyr Ala Lys Lys Ser Tyr Pro Glu Lys Ser His Pro Glu Lys Ser
            450                 455                 460

Tyr Pro Glu Lys Ser His Pro Glu Lys Ser Tyr Pro Glu Lys Ser His
465                 470                 475                 480

Pro Glu Lys Ser Tyr Asp Glu Gln Ala Glu Ala Glu Lys Val Lys Glu

```
                      485                 490                 495
Glu Ser Lys Glu Lys Ala Tyr Pro Val Ser His Ser Ile Ser Ser His
            500                 505                 510

Gly Ser Ile Ala Ala Asp Thr Ala Phe Leu Glu Asn Leu Asp Trp Glu
            515                 520                 525

Thr Leu Val His Glu Asn Leu Pro Gly Leu Met Asp Met Asp Gln Asp
            530                 535                 540

Asp Arg Ile Val Trp Pro Arg Asp Ser Leu Phe Arg Tyr Phe Glu Leu
545                 550                 555                 560

Leu Glu Lys Leu Gln Tyr Asn Leu Glu Glu Arg Lys Lys Leu Gln Glu
                565                 570                 575

Phe Ala Val Gln Ala Leu Met Ser Phe Glu Asp Lys
                580                 585

<210> SEQ ID NO 7
<211> LENGTH: 235
<212> TYPE: PRT
<213> ORGANISM: Mus musculus

<400> SEQUENCE: 7

Met Ile Leu Ser Leu Thr Gln Ser Leu Gly Phe Glu Thr Phe Ile Phe
  1               5                  10                  15

Ile Val Val Cys Leu Asn Thr Val Ile Leu Val Ala Gln Thr Phe Thr
                 20                  25                  30

Glu Leu Glu Ile Arg Gly Glu Trp Tyr Phe Met Val Leu Asp Ser Ile
             35                  40                  45

Phe Leu Ser Ile Tyr Val Leu Glu Ala Val Leu Lys Leu Ile Ala Leu
         50                  55                  60

Gly Leu Glu Tyr Phe Tyr Asp Pro Trp Asn Asn Leu Asp Phe Phe Ile
 65                  70                  75                  80

Met Val Met Ala Val Leu Asp Phe Val Leu Gln Ile Asn Ser Leu
                 85                  90                  95

Ser Tyr Ser Phe Tyr Asn His Ser Leu Phe Arg Ile Leu Lys Val Phe
                100                 105                 110

Lys Ser Met Arg Ala Leu Arg Ala Ile Arg Val Leu Arg Arg Leu Ser
            115                 120                 125

Ile Leu Thr Ser Leu His Glu Val Ala Gly Thr Leu Ser Gly Ser Leu
            130                 135                 140

Pro Ser Ile Thr Ala Ile Leu Thr Leu Met Phe Thr Cys Leu Phe Leu
145                 150                 155                 160

Phe Ser Val Val Leu Arg Ala Leu Phe Gln Asp Ser Asp Pro Lys Arg
                165                 170                 175

Phe Gln Asn Ile Phe Thr Thr Leu Phe Thr Leu Phe Thr Met Leu Thr
                180                 185                 190

Leu Asp Asp Trp Ser Leu Ile Tyr Ile Asp Asn Arg Ala Gln Gly Ala
                195                 200                 205

Trp Tyr Ile Ile Pro Ile Leu Met Ile Tyr Ile Val Ile Gln Tyr Phe
            210                 215                 220

Ile Phe Leu Asn Leu Val Ile Ala Val Leu Val
225                 230                 235
```